United States Patent
Sinha et al.

(10) Patent No.: US 9,914,745 B2
(45) Date of Patent: Mar. 13, 2018

(54) MORPHOLINO-BASED ANTISENSE AGENT

(75) Inventors: Surajit Sinha, Kolkata (IN); Sankha Pattanayak, Kolkata (IN); Sibasish Paul, Kolkata (IN); Bappaditya Nandi, Kolkata (IN)

(73) Assignee: INDIAN ASSOCIATION FOR THE CULTIVATION OF SCIENCE, Kolkata (IN)

( * ) Notice: Subject to any disclaimer, the term of this patent is extended or adjusted under 35 U.S.C. 154(b) by 95 days.

(21) Appl. No.: 13/390,348

(22) PCT Filed: Aug. 10, 2010

(86) PCT No.: PCT/IN2010/000529
§ 371 (c)(1),
(2), (4) Date: Feb. 14, 2012

(87) PCT Pub. No.: WO2011/018798
PCT Pub. Date: Feb. 17, 2011

(65) Prior Publication Data
US 2012/0296087 A1   Nov. 22, 2012

(30) Foreign Application Priority Data
Aug. 14, 2009   (IN) .......................... 1059/KOL/2009

(51) Int. Cl.
| | | |
|---|---|---|
| *C07D 413/14* | (2006.01) | |
| *C07D 413/04* | (2006.01) | |
| *C07F 7/18* | (2006.01) | |
| *C07F 9/6558* | (2006.01) | |
| *C07F 9/6533* | (2006.01) | |
| *C12N 15/11* | (2006.01) | |
| *C12N 15/113* | (2010.01) | |

(52) U.S. Cl.
CPC ........ *C07F 9/65583* (2013.01); *C07F 9/6533* (2013.01); *C07F 9/65586* (2013.01); *C12N 15/111* (2013.01); *C12N 15/113* (2013.01); *C12N 2310/11* (2013.01); *C12N 2310/3233* (2013.01); *C12N 2320/51* (2013.01)

(58) Field of Classification Search
CPC ................ C07F 9/6533; C07F 9/65583; C07F 9/65586; C12N 15/113; C12N 15/111; C12N 2320/51; C12N 2310/11; C12N 2310/3233
USPC ............................................ 544/69, 123, 79
See application file for complete search history.

(56) References Cited

U.S. PATENT DOCUMENTS

| | | |
|---|---|---|
| 2,269,892 A | 1/1942 | Carter |
| 5,698,685 A | 12/1997 | Summerton et al. |
| 6,124,271 A | 9/2000 | Iversen et al. |
| 7,943,762 B2 * | 5/2011 | Weller et al. .................. 536/31 |
| 2005/0176948 A1 | 8/2005 | Gouliaev et al. |
| 2009/0088562 A1 | 4/2009 | Weller et al. |
| 2009/0123372 A1 | 5/2009 | Kolb et al. |

OTHER PUBLICATIONS

Dempcy et al. Design and synthesis of deoxynucleic guanidine: A polycation analogue of DNA. Proc Natl Acad Sci USA 91:7864-7868, 1994.*
Perez-Rentero et al. Novel oligonucleotide analogues containing a morpholinoamidine unit. Tetrahedron 65 (2009) 1171-1179.*
International Search Report for PCT/IN/00529, dated Feb. 2011.

* cited by examiner

*Primary Examiner* — Yih-Horng Shiao
(74) *Attorney, Agent, or Firm* — The PL Law Group, PLLC

(57) ABSTRACT

Morpholino-based oligomers suitable as antisense agent comprising modifications of phosphorodiamidate backbone or modification with 5-substituted pyrimidines of morpholino compound that is soluble in culture medium and sufficient for cell penetration thereby eliminating the need for injecting into the cells. Monomers comprising the said oligomers and its method of manufacture, method of manufacture of the said oligomers and its dye, fluorophore, drug, biomolecule conjugate wherein the said oligomers find different end use but not limited to regulation of gene expression, tissue culture with improved transfection efficiency and related studies on cellular transfection.

5 Claims, 17 Drawing Sheets

Morpholino oligomer

7'-Azido cationic morpholino (tetramer)

7'-Fluorescein-conjugated cationic morpholino

7'-Azido-4'-fluorescein-conjugated
cationic morpholino

Type 1, partially cationic morpholino, incorporation of the cationic charge in the backbone Type 2: Cationic charge incorporated into the pyrimidine bases through introduction by -NH$_2$ or guanidinium group at 5-position.

Type 3: Alkynyl-or alkyl- substituted morpholino oligos, when R = -CH$_2$CH$_3$

Type 2: 7'-Azido-4'-fluorescein-conjugated cationic morpholino, cationic charges incorporated by the 5- substitution on the pyrimidine bases through $NH_2$ or guanidinium groups.

Type 3: 7'-Azido neutral morpholino, pentyne or pentyl groups incorporated by the 5- substitution on the pyrimidine bases.

(Monomer unit)

7'-Activated-Monomer, 9a, 9b, 9c & 9d
when B = A, G, C, T, respectively

T-Morpholino, 10a    A-Morpholino, 11a    C-Morpholino, 12a    G-Morpholino, 13a (Monomer unit with 7'-NH$_2$)

7'-Activated-Monomer
(thiourea-derivative), 14

R = NHCOCF$_3$ or ethyl    Trit = Triphenylmethyl-    R' = NHCOCF$_3$ or ethyl
B = U or C(N$^4$-Ac)

7'-Activated-Monomer

5-Iodo monomer

General route for the synthesis of protected morpholino monomers.

Synthetic scheme for 7'-amino morpholino monomers

FIG. 18
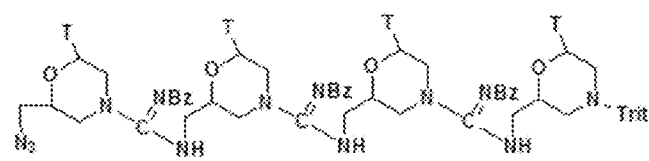
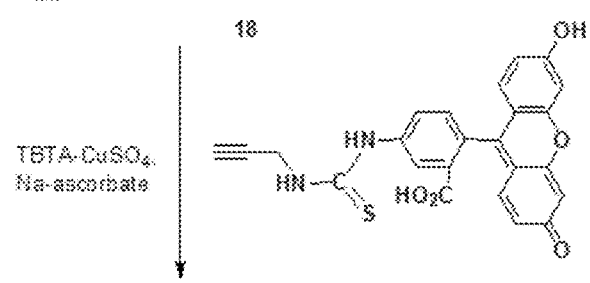
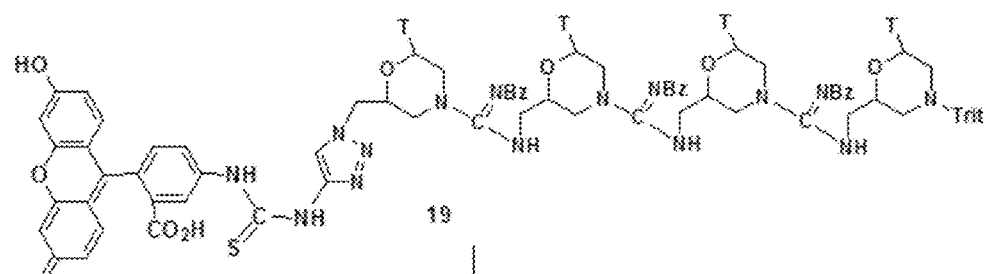
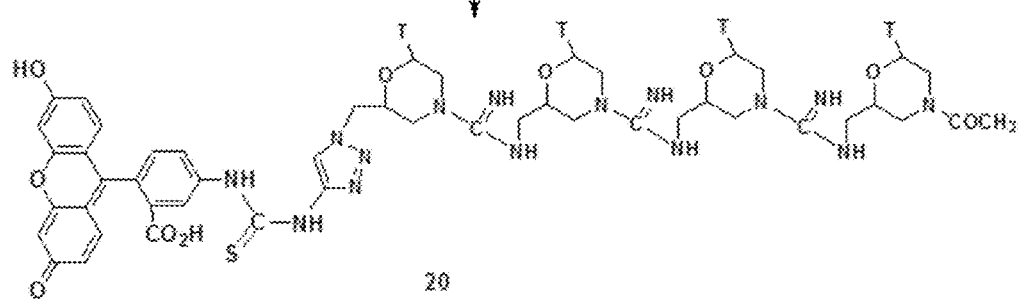
7'-Fluorophore-conjugated cationic morpholino 7'-Azido-4'-fluorophore-conjugated cationic morpholino Synthesis of morpholino Oligomer according to
US Patent 5185444 by Gene Tools LLC and
Nature Chemical Biology 2007, 3, 650 by Chen et al Synthesis of T$_8$-morpholino oligos Synthesis of partially cationic morpholino oligos, Type 1

Synthesis of 5-iodo and 5-substituted pyrimidines

MORPHOLINO-BASED ANTISENSE AGENT

CROSS REFERENCE TO RELATED APPLICATION

The present application claims priority to International Application PCT/IN2010/000529 filed on Aug. 10, 2010, which claims priority to IN 1059/KOL/2009 filed on Aug. 14, 2009, the entire contents of which are incorporated herein by reference.

FIELD OF INVENTION

The present invention relates to morpholino-based antisense agents and, more particularly, morpholino-based antisense agent comprising cationic inter-subunit linkage in the oligonucleotide backbone and cationic side chains to the nucleotide bases and a simple and cost-effective method for the synthesis of the same. Specifically, the said morpholino-based antisense agents of the present invention facilitates in achieving improved functional attributes with regard to better transfection efficiency in terms of higher activity and selectivity. Importantly and more specifically, the morpholino-based antisense agents of the present invention are found to remain soluble in culture medium and sufficient for cell penetration thus eliminating the need for injecting the said antisense agents into the cells. Advantageously, the present invention is also directed to a wide scale application of the said cationic/partially cationic/completely neutral morpholino based oligomers for its different end use including but not limited to regulation of gene expression, tissue culture with improved transfection efficiency and related studies on cellular transfection. Additionally, the present invention is also directed to partially cationic morpholino based oligomer-dye, fluorophore, drug etc. conjugates and its method of synthesis. The present invention is further directed to morpholino monomers and its process of synthesis thereof.

BACKGROUND ART

Antisense technologies are a suite of techniques that, together, form a very powerful weapon for studying gene function (functional genomics) and for discovering new and more specific treatments of diseases in humans, animals, and plants (antisense therapeutics). A conventional definition of antisense refers to the laboratory manipulation and/or modification of DNA or RNA so that its components (nucleotides) form a complementary copy of normal, or "sense," messenger RNA (mRNA). The binding, or hybridization, of antisense nucleic acid sequences to a specific mRNA target will, through a number of different mechanisms, interrupt normal cellular processing of the genetic message of a gene. This interruption, sometimes referred to as "knock-down" or "knock-out" depending upon whether or not the message is either partially or completely eliminated, allows researchers to determine the function of that gene.

One of the significant problems faced by developmental biologists, who do not work on an organism with well developed genetics and even for some who do, is how to inhibit the action of a gene of interest during its developmental process so as to learn about its normal biological functions. A widely accepted approach is to use the antisense technologies.

C. Cazenave, et al. in Nucleic Acids Res. 1989, 17, 4255 is directed to the first generation antisense oligonucleotides that were designed as short stretches of DNA (18-22mers) that form RNA-DNA hybrids with the target mRNA and act as substrates for RNase H to degrade the mRNA. The target mRNA is cleaved by RNase H and the fragments are subsequently broken down by nuclease activity. DNA oligonucleotides have had very limited applicability in developmental studies, both because they have non-specific toxic side effects and because degraded mRNAs are continually replaced by new transcription, making continued treatment with oligonucleotides a necessity.

Studies from a number of laboratories suggest that morpholino based oligonucleotides can be microinjected into zebrafish (Nasevicius, A. and Ekker, S. C. Nat. Genet. 2000, 26, 216), sea urchin (Eisen, J. S.; Smith, J. C. Development 2008, 135, 1735) or xenopus embryos (Coffman, J. A. et. al. Runx gene. BMC Biol. 2004, 2, 6), where they block gene expression and produce phenotypic effects during the early stage of embryogenesis. It is known in the art that light mediated activation of morpholino enables spatio-temporal regulation of ntl gene expression during zebrafish embryogenesis. The strengths of morpholinos as a tool for investigating vertebrate development is well described in a recent review by Ekker (Ekker, S. C. Morphants Yeast 2000, 17, 302). The greatest advantage is that phenotypes can be rapidly observed in animal models using a relatively inexpensive method. Ekker and colleagues also reported inhibition of several endogenous zebrafish gene and have compiled a database (The Morphant database) thereof detailing the phenotypes produced by morpholino oligonucleotides. Since then morpholinos have become superior agents for gene inhibition relative to other types of oligomers that might block translation, such as locked nucleic acid (LNA), peptide nucleic acid (PNA) or 2'-modified RNA.

Morpholino antisense oligomers taught in U.S. Pat. No. 5,185,444 and U.S. Pat. No. 5,034,506, are chemically modified nucleotides, widely used in gene regulation studies that cost about US$500-600 for 300 nanomol. The said morpholino-based oligomers block mRNA translation in binding 5' UTR region, overcoming many of the limitations of regular DNA oligonucleotides.

The drawbacks in employing the above said morpholino based oligomers in developmental biology lies in the chiral nature of the morpholino phosphorodiamidate backbones that complicates their synthesis and purification. Further, adding an additional hurdle to the poor Morpholino transfection properties is the neutrality of its backbone comprising of phosphorodiamidate moiety that poses a serious limitation for use of these oligomers in tissue culture as well as in vivo studies. Accordingly, the delivery of morpholino into embryos requiring microinjection procedures, PNA (peptide nucleic acid) analogs constitute an alternative approach but they also have very limited applications due to their poor solubility in water under physiological conditions as taught in K. A. Urtishak, et. al., Dev. Dynamics; 228, 405, 2003.

Again to overcome the cellular transfection property of such morpholine based oligomers, M. H. Nelson, et al. in Bioconjug. Chem. 2005, 16, 959 and U.S. Pat. No. 7,468, 418 illustrates the incorporation of cationic charge onto the morpholino oligomer through the conjugation with the arginine-rich peptide to study the effects on antisense activity and specificity. Although the insertion of cationic charge into the morpholino oligomers improved the antisense efficiency, however incorporation of arginine peptides for optimized results were found to be procedurally difficult and non-reproducible to the fullest extent. Furthermore, the structure of the morpholino oligomer of the above said prior art was not structurally modified wherein the product is a just a simple conjugate comprising a carrier peptide attached to a nucleic acid analog comprising a substantially uncharged backbone and a targeting base sequence.

Reference is drawn to WO/2008/036127 that teaches a morpholino oligomer containing both uncharged and cationic intersubunit linkages. The oligomers are oligonucleotide analogs containing predetermined sequences of base-pairing moieties. The presence of the cationic intersubunit linkages in the oligomers, typically at a level of about 10-50% of total linkages, provide enhanced antisense activity, in various antisense applications, relative to the corresponding uncharged oligomers. Also provided are such oligomers conjugated to peptide transporter moieties, where the transporters are preferably composed of arginine subunits, or arginine dimers, alternating with neutral amino acid subunits. The said oligomers having an uncharged backbone, the cationic substitution takes place in the side chain associated with the phosphorodiamidate linkage, therefore the transfection efficiency is moderate and the product is costly because of the troublesome process of preparation.

J. Yuan, et al. in J. Virol. 2006, 80, 11510 illustrates peptide-conjugated morpholino oligomers targeting the internal ribosome entry site, in which morpholino have been conjugated to various cell-penetrating peptides (CPPs) in order to enhance both morpholino uptake into cells and antisense efficacy (M. H. Nelson, et al. Arginine-rich peptide conjugation to morpholino oligomers: effects on antisense activity and specificity. Bioconjug. Chem. 2005, 16, 959). The conjugated morpholinos has a better binding ability to complimentary RNA in reduced length of 14 bases from 20 bases. Though Arginine peptide conjugated morpholino have demonstrated considerable efficacy against a number of RNA viruses including foot-and-mouth disease virus (A. Vagnozzi, et. al. in J. Virol. 2007, 81, 11669) in cell cultures and against Ebola virus, West Nile virus, murine corona viruses, and CVB3 in both cell culture and animal models, the limitations of such arginine rich peptide conjugated morpholino oligomers lies in its poor solubility in tissue culture media and complicated process of synthesis thereof.

It is thus clearly apparent from the above discussions that though modifications of the morpholino oligomers are known in the art, they suffer from serious drawbacks such as cumbersome synthetic procedures, poor solubility and reduced antisense efficacy.

Thus to address the need of the day there remains a long felt need in the art to bring about structural modifications in the above said morpholine oligomers through simple and cheap synthetic pathway to overcome the above said drawbacks by accomplishing improved antisense efficacy and increased solubility of such oligomers.

OBJECTS OF THE INVENTION

It is thus the basic object of the present invention to provide for new and improved morpholino-based antisense agent and method of synthesis thereof.

Another object of the invention is to provide for an easy and cost-effective synthetic method for the synthesis of new and improved morpholino-based anti-sense agents including monomers with cationic backbone and partially cationic substituted bases of morpholino compound that is fast and require lesser number of ingredients to reach to the product of the invention.

Another object of the present invention is to provide a synthetic method for the preparation of alkynyl- and alkyl-substituted morpholino compound.

Yet another object of the invention is to provide for a viable synthetic method for the development of functionalized cationic morpholino oligomers having higher activity and selectivity with regard to better transfection efficiency than the ones already known in the art.

Yet another object of the invention is to provide morpholino oligomers by the addition or incorporation of guanidinium group to the morpholino unit or to the pyrimidine bases as well and includes the bases with the side chain of free amino groups ($-NH_2$).

Yet another object of the invention is to provide synthesis of cationic morpholino-conjugates with various molecules for biological application and study their cellular transfection properties.

Yet further object of the present invention is directed to provide for cationic morpholino-conjugates with dyes, fluorophore and drug and its method of synthesis thereof for the study of their cellular transfection properties.

It is a further object of the present invention to provide for improved cationic morpholino-based antisense agent that is soluble in culture medium and is sufficient far cell penetration thus eliminating the need for injecting the antisense agents into the cells.

Still further object of the present invention is to provide for improved cationic morpholino-based antisense agent that would result in more specific gene regulation.

Yet another object of the present invention is to enhance the morpholino cellular transfection properties by replacing the neutrality of its backbone with a positive charged backbone that would not pose any limitation for tissue culture and other in-vivo studies.

It is yet a further object of the present invention to provide for cationic morpholino oligos that would not necessitate its conjugation with arginine-rich peptides to therefore eliminate the need to be injected into the cells.

It is another object of the present invention to provide for a new synthetic methodology for the synthesis of new class of morpholino monomers.

SUMMARY OF THE INVENTION

Thus according to the basic aspect of the invention there is provided morpholino based oligomers suitable as antisense agents comprising:

anyone or more of (i) modified cationic backbone involving atleast partial replacement of some of the phosphorodiamidate linkage with cationic (positive) charge with or without the incorporation of anyone or more of alkynyl, alkyl, amine and guanidinium groups into the purine, pyrimidine bases of the morpholino unit (ii) neutral backbone involving at least partial cationic charges introduced intermittently through a $NH_2$ group or a guanidinium group into the purine, pyrimidine bases of the morpholino unit and/or partial cationic charge introduced intermittently through a $NH_2$ group or a guanidinium group into the purine, pyrimidine bases of the morpholino unit with intermittent incorporation of alkynyl and alkyl groups into purine, pyrimidine bases of the remaining morpholino units of the neutral backbone and/or incorporation of cationic charges by $NH_2$ group or a guanidinium group into all the said purine, pyrimidine bases in all the morpholino units of the neutral backbone and (iii) neutral backbone incorporating alkynyl and alkyl groups into the purine, pyrimidine bases of the morpholino unit.

In another preferred aspect of the invention in the said morpholino based oligomers suitable as antisense agents, the said cationic backbone of the oligomer includes guanidinium linkage.

In yet another preferred aspect of the invention there is provided said morpholino based oligomers which are soluble in culture medium and sufficient for cell penetration on its own.

In another aspect of the invention there is provided said morpholino based oligomers wherein the said (i) modified cationic backbone of said oligomer comprises of monomers preferably selected from as hereunder:

(Monomer unit with 7'-NH₂)

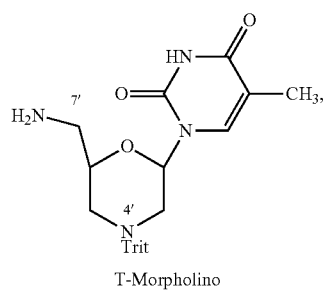

T-Morpholino

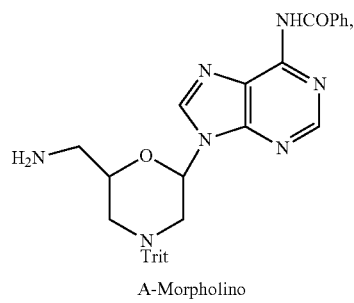

A-Morpholino

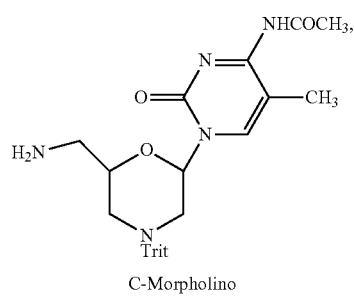

C-Morpholino

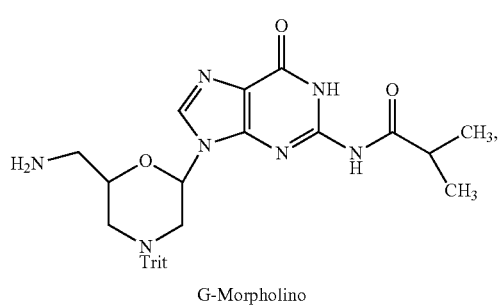

G-Morpholino

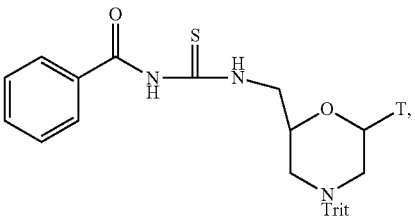

7'-Activated-Monomer
(thiourea-derivative)

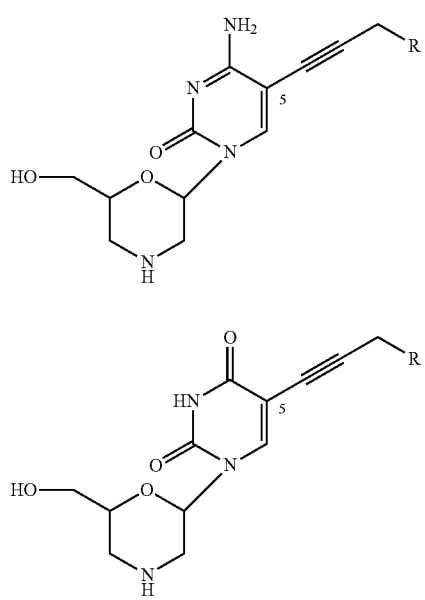

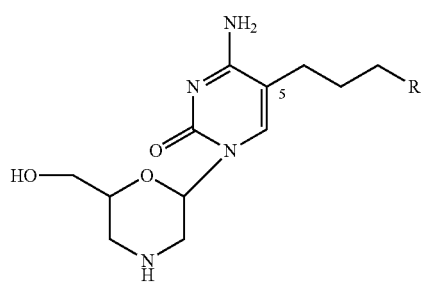

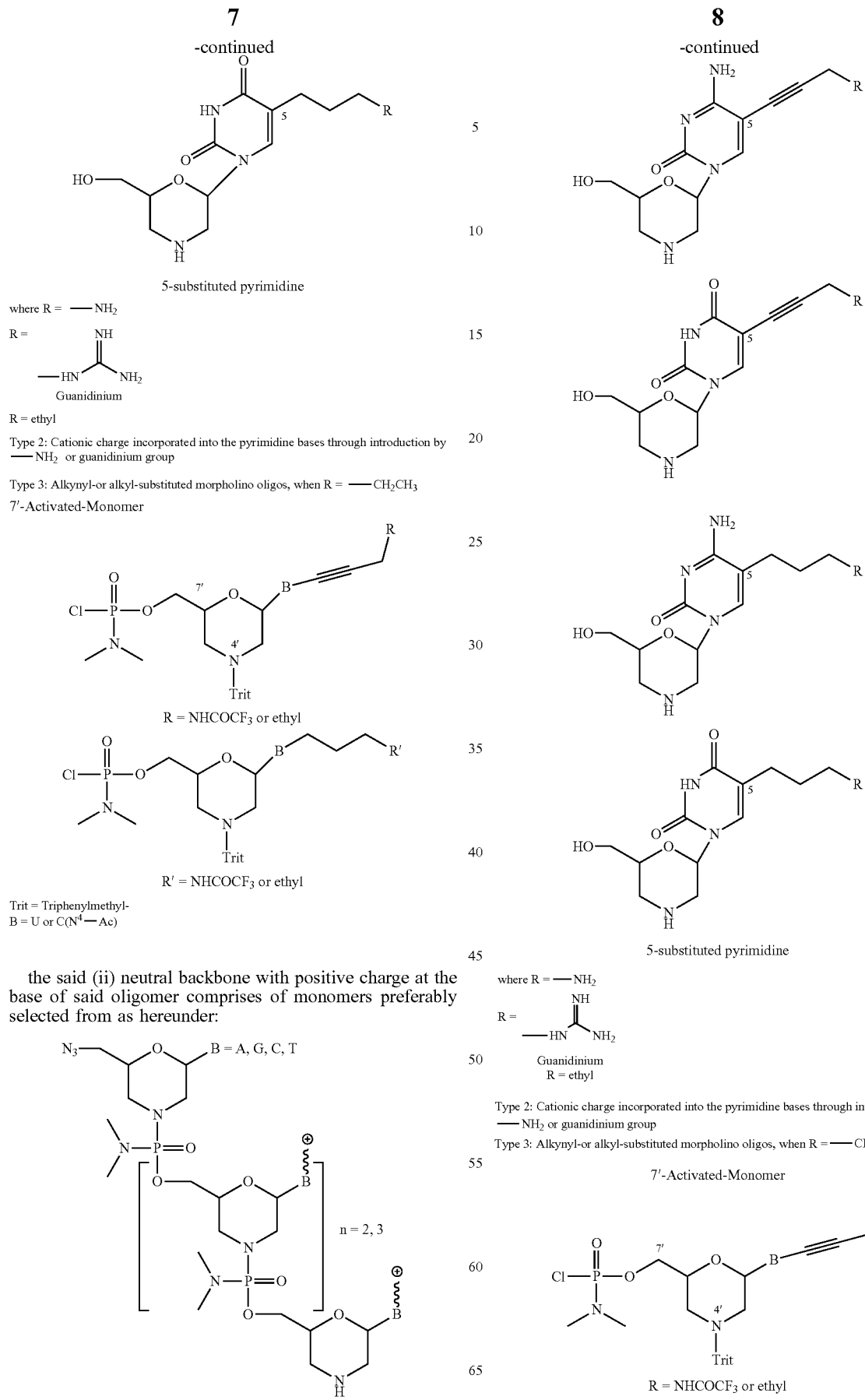

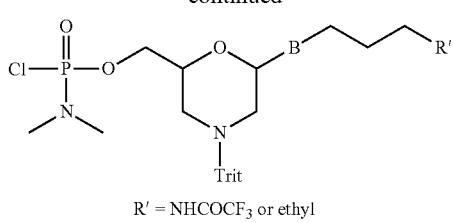

R' = NHCOCF₃ or ethyl

Trit = Triphenylmethyl-
B = U or C(N⁴—Ac)

the said (iii) neutral backbone with neutral group at the base of said oligomer comprises of monomers preferably selected from as hereunder:

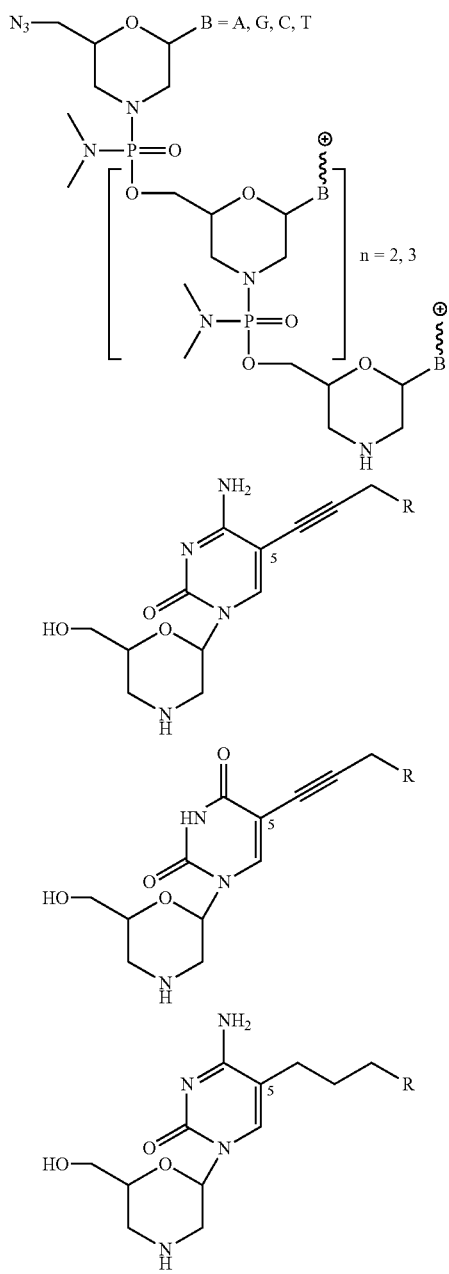

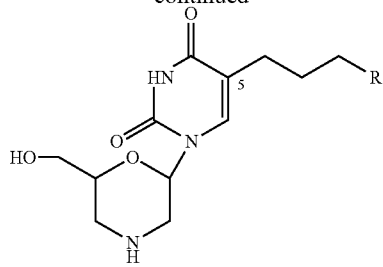

5-substituted pyrimidine where R = —NH₂

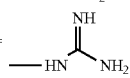

Guanidinium
R = ethyl

Type 2: Cationic charge incorporated into the pyrimidine bases through introduction by —NH₂ or guanidinium group Type 3: Alkynyl-or alkyl-substituted morpholino oligos, when R =—CH₂CH₃

7'-Activated-Monomer

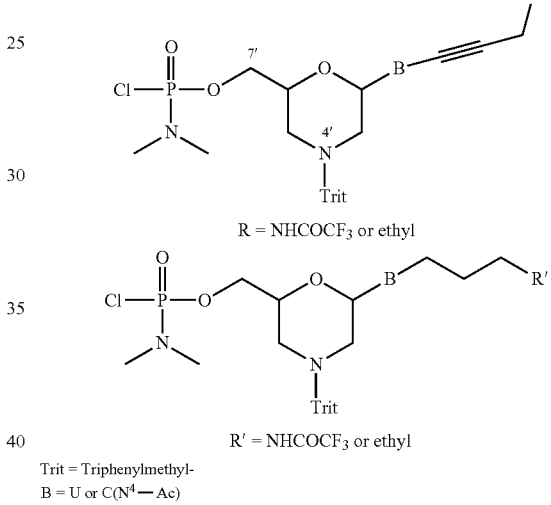

R = NHCOCF₃ or ethyl

R' = NHCOCF₃ or ethyl

Trit = Triphenylmethyl-
B = U or C(N⁴—Ac)

In yet another aspect of the present invention there is provided a method for the manufacture of morpholino based oligomers under abovesaid situation (i) involving total replacement of the neutral phosphorodiamidate linkage with cationic (positive) charge preferably with guanidinium linkage comprising the steps of:

a) deprotecting the 4'-N-trityl group of the 7'-azide purine and pyrimidine based N-trityl morpholino monomers with 10% HOAc in TFE and evaporating the solvent to yield a residue;

b) dissolving the said residue in DMF and adding to it the thiourea derivatized active purine and pyrimidine based 4'-N-trityl morpholino monomers and diisopropylethylamine (DIEA) followed by cooling at 0° C.;

c) adding a solution of HgCl₂ in dry DMF dropwise to the solution of step (b) above resulting in an instant cloudy white precipitate;

d) diluting with methanol, filtering and evaporating it in vacuo to obtain the dimer therefrom;

e) repeating the same said reaction sequence of deprotection and coupling to obtain the trimer, tetramer and oligomer therefrom.

In another aspect of the present invention there is provided a method for the manufacture of said morpholino based oligomers also under abovesaid situation (i) involving partial replacement of the phosphorodiamidate linkage with cationic (positive) charge preferably guanidinium linkage comprising the steps of:

a) reacting the neutral morpholino oligomer preferably 8-mer with N-hydroxysuccinimide ester of hexynoic acid in the presence of $Et_3N$ in DMF and obtaining 4'-alkyne terminated neutral morpholino 8-mer;

b) reacting the 7'-azide terminated cationic 4'-N-trityl morpholino oligomer with 4'-alkyne terminated neutral morpholino 8-mer via click reaction in the presence of TBTA-$CuSO_4$, Na-ascorbate;

c) drying the reaction mixture and purifying it over the cation exchange resin column preferably a Dowex column and obtaining the said partially cationic morpholino conjugated fluorophore oligomer therefrom.

In yet another aspect of the present invention there is provided a method for the manufacture of said morpholino based oligomers with neutral backbone under abovesaid situation (ii) involving cationic charge on few purine, pyrimidine bases of the morpholino units with intermittent alkyne and alkyl terminated purine, pyrimidine based morpholine units and/or cationic charge incorporated in all the purine, pyrimidine bases of the morpholino units with neutral phosphorodiamidate backbone comprising the steps of:

a) reacting at least one or more of 7'-chlorophosphoramidate activated-4'-N-trityl-$NH_2$ group or guanidinium group terminated purine, pyrimidine morpholino unit and alkyne/alkyl terminated purine, pyrimidine morpholino unit with 7'-azide-4'-free pyrimidine or purine based morpholino unit in presence of $Et_3N$ to yield a 7'-azide-4'-N-trityl morpholino dimer;

b) deprotecting the trityl group by treatment with 4% HOAc/TFE of the said dimer and further reacting with at least one or more of 7'-chlorophosphoramidate activated $NH_2$ group or guanidinium group terminated purine, pyrimidine morpholino unit or alkyne/alkyl terminated purine, pyrimidine morpholino unit in presence of $Et_3N$ to yield a 7'-azide-4'-N-trityl morpholino trimer;

c) repeating the above reaction sequence to obtain an 7'-azide-4'-N-trityl oligomer preferably 5-mer;

d) detritylation by 4% HOAc in TFE followed by acetylation by acetic anhydride/$Et_3N$ and deprotection of trifluoroacetyl groups of the protected amine side chain of the purine and pyrimidine based morpholino oligos by $K_2CO_3$, MeOH, $H_2O$ (1:1) further purifying through a cation exchange resin to obtain the said ologomers under situation (ii) therefrom.

In yet another aspect of the present invention there is provided a method for the manufacture of said morpholino based oligomers with neutral backbone under abovesaid situation (iii) incorporating alkynyl and alkyl groups into the purine, pyrimidine bases of the morpholino unit comprising the steps of:

a) reacting at least one or more of 7'-chlorophosphoramidate activated-4'-N-trityl-alkyne/alkyl terminated purine, pyrimidine morpholino unit with 7'-azide-4'-free pyrimidine or purine based morpholino unit in presence of $Et_3N$ to yield a 7'-azide-4'-N-trityl morpholino dimer;

b) deprotecting the trityl group by treatment with 4% HOAc/TFE of the said dimer and further reacting with at least one or more of 7'-chlorophosphoramidate activated alkyne/alkyl terminated purine, pyrimidine morpholino unit in presence of $Et_3N$ to yield a 7'-azide-4'-N-trityl morpholino trimer;

c) repeating the above reaction sequence to obtain an 7'-azide-4'-N-trityl oligomer preferably 5-mer;

d) detritylation by 4% HOAc in TFE followed by acetylation by acetic anhydride/$Et_3N$ to obtain the oligomer under situation (iii) therefrom.

Preferably, the said morpholino based oligomers suitable as antisense agents involves length of the said oligomers of upto 25 mers that does not affect the Watson-Crick base pairing, has higher activity and selectivity and avoids the need of conjugation with arginine rich peptides.

More preferably, the said morpholino based oligomers suitable as antisense agents comprises said oligomer conjugated at the 4' end and/or the 7' end selectively with biomolecules, drugs, or dyes such as fluorophores adapted to facilitate cellular transfection properties and facilitate in monitoring transfection efficiency.

In another preferred aspect of the invention there is provided a method for the manufacture of 7'-fluorophore conjugated-4' N-acetyl-modified cationic backbone based morpholino oligomers comprising the steps of:

a) adding the 7' azido 4'-trityl guanidinium backbone based morpholino tetramer to a solution of propargyl amine containing FITC followed by the addition of TBTA-$CuSO_4$, in DMSO and Na-ascorbate in water and stirring;

b) removing the solvent in vacuo and purifying the fluorophore conjugate obtained from step (a) above using preparative TLC;

c) deprotection of the 4'-trityl group of the said fluorophore conjugate with 10% HOAc in TEE and removing the solvent in vacuo;

d) protecting the free 4'-NH group of the said fluorophore conjugate obtained from step (c) above with acetyl group using acetic anhydride and triethylamine;

e) deprotecting the benzoyl groups from the guanidinium backbone by $K_2CO_3$, MeOH and water, purifying in HPLC and obtaining the said 7'-fluorophore-Conjugated 4' N-acetyl modified cationic backbone based morpholino oligomers preferably guanidinium backbone based cationic morpholino therefrom.

In yet another preferred aspect of the invention there is provided a method for the manufacture of 7'-azido-4'-fluorophore-conjugated modified cationic backbone based morpholino oligomers comprising the steps of:

a) deprotecting the trityl group of 7' azido 4'-trityl guanidinium backbone based morpholino tetramer by 10% HOAc in TFE and removing the solvent to obtain a residue;

b) dissolving the said residue in DMF and reacted with N-trifluoroacetyl aminocaproic acid N-hydroxysuccinimide ester (1.2 mg, 3.7 µmol) in the presence of $Et_3N$ and obtaining the 7'-azido-4'-protected amide of guanidinium backbone based cationic morpholino and purifying it;

c) deprotecting the benzoyl of guanidinium linkage and the trifluoroacetyl of the 4' amide group in the presence of 5% $K_2CO_3$ in MeOH and water;

d) reacting the solution obtained from step (c) above with FITC in the presence of triethylamine, purifying it through HPLC and obtaining the said 7'-azido-4'-fluorophore-conjugated modified cationic backbone based morpholino oligomers preferably guanidinium backbone based cationic morpholino therefrom.

In a preferred aspect of the invention there is provided a method for the manufacture of 4'-N-fluorophore conjugated partially cationic backbone based morpholino oligomer involving the conjugation of cationic fluorophore conjugated morpholino with neutral morpholino and Comprising the steps of:

a) reacting the neutral morpholino oligomer preferably 8-mer with N-hydroxysuccinimide ester of hexynoic acid in the presence of Et₃N in DMF and obtaining 4'-alkyne terminated neutral morpholino 8-mer;

b) reacting the 7'-azide terminated cationic backbone based 4'-N-fluorophore conjugated morpholino oligomer with 4'-alkyne terminated neutral backbone based morpholino 8-mer via click reaction in the presence of TBTA-CuSO₄, Na-ascorbate;

c) drying the reaction mixture and purifying it over the cation exchange resin column preferably a Dowex column and obtaining the said partially cationic morpholino conjugated fluorophore oligomer therefrom.

In still another preferred aspect of the invention there is provided a method for the manufacture of 4'-N-fluorophore conjugated neutral backbone based morpholino oligomer involving introduction of cationic charge by guanidinium group to the pyrimidine bases comprising the steps of:

a) reacting the 7'-azide-4'-N-trityl-free amine terminated pyrimidine based morpholino oligomer preferably 5-mer with K₂CO₃ in MeOH/H₂O in the presence of pyrazole hydrazine hydrochloride to obtain the pyrimidine guanidinium terminated 7'-azide-4'-N-trityl-morpholino oligomer;

b) deprotecting the trityl group by treatment with 4% HOAc/TFE;

c) dissolving the 7'azide-4' deprotected oligomer obtained from step (c) in DMF/Et₃N mixture and treating with N-trifluoroacetyl-amino caproic acid N-hydroxysuccinimide ester to obtain the 7'-azide-4'-trifluoroacetyl amide terminated oligomer;

d) reacting the said 4'-trifluoroacetyl amide terminated oligomer with FITC and purifying with cation exchange resin to obtain the said guanidinium terminated pyrimidine based morpholino oligomers conjugated with fluorophore at its 4'-end.

In yet another most preferred aspect of the invention there is provided a method for the manufacture of 4'-N fluorophore-7'-biomolecule and/or drug conjugated morpholino oligomer preferably of neutral backbone comprising the steps of:

a) reacting the 7'-azide-4'-N-fluorophore conjugated neutral backbone based morpholino oligomer with a drug or biomolecule at its 7'-azide end b) obtaining the said 4'-N fluorophore conjugated 7'-conjugated biomolecule or drug conjugated based oligomer therefrom.

In another preferred aspect of the invention there is provided morpholino based monomers of the type as represented hereunder:

(Monomer unit)

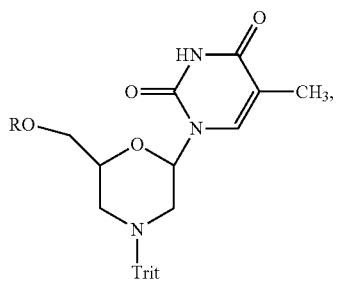

T-Morpholino
1: R = TBDPS
1a: R = H

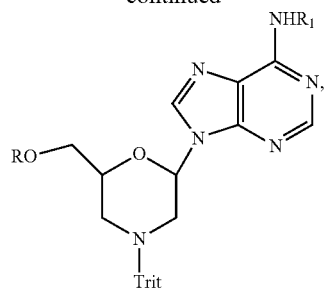

A-Morpholino
2: R = TBDPS; R₁ = H
2a: R = TBDPS; R₁ = Bz
2b: R = H; R₁ = Bz

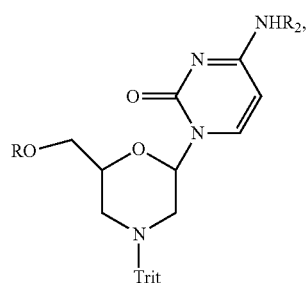

C-Morpholino
3: R = TBDPS; R₂ = H
3a: R = TBDPS; R₂ = Ac
3b: R = H; R₂ = Ac

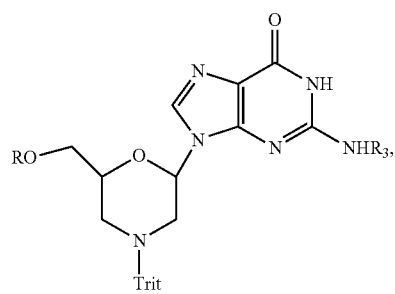

G-Morpholino
4: R = TBDPS; R₃ = H
4a: R = TBDPS; R₃ = ⁱBu
4b: R = H; R₂ = ⁱBu

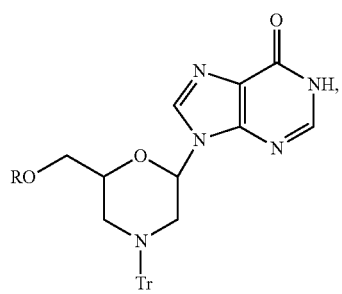

Inosine (I)-Morpholino
5: R = TBDPS
5a: R = H

-continued

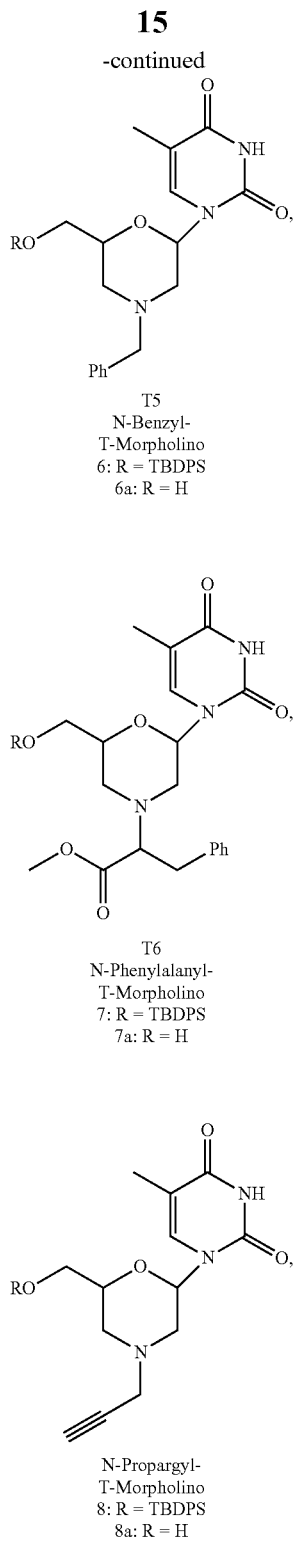

T5
N-Benzyl-
T-Morpholino
6: R = TBDPS
6a: R = H

T6
N-Phenylalanyl-
T-Morpholino
7: R = TBDPS
7a: R = H

N-Propargyl-
T-Morpholino
8: R = TBDPS
8a: R = H

Trit = Triphenylmethyl-
$R_1 =$ —COPh (Bz)
$R_2 =$ —COCH$_3$(Ac)
$R_3 =$

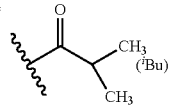

R = OH, tert-butyl-diphenylsilyl (TBDPS)

-continued

5-Iodo monomer

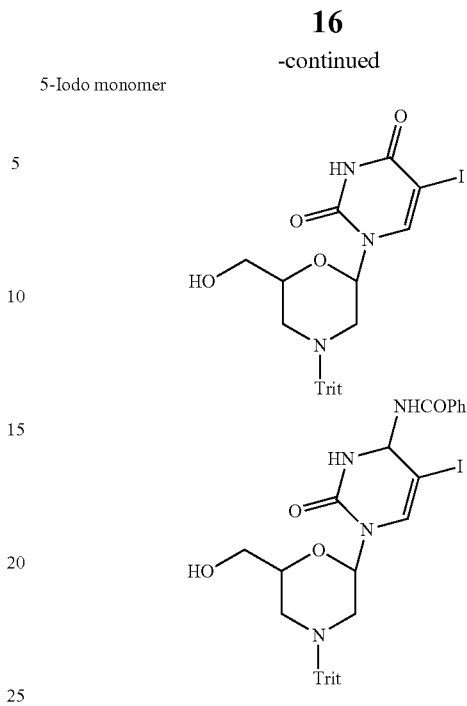

Preferably, the above said morpholino based monomers are adapted to be functionalized suitable for morpholino based oligomers as antisense agents.

In another preferred aspect of the invention there is provided a process for the synthesis of pyrimidine and purine based N-trityl, 7'-TBDPS (Tert-butyl-diphenylsilyl) protected morpholino monomer comprising the steps of:

a) Adding imidazole and TBDPSCl dropwise to a stirred solution of the nucleoside in dry DMF under inert atmosphere;

b) stirring and noting the disappearance of the starting material followed by the addition of methanol;

c) stirring and evaporation of the solvent under reduced pressure to yield the 5'-protected nucleoside;

d) dissolving the said 5'-protected nucleoside in methanol by heating on a water bath cooling and adding sodium meta-periodate and ammonium biborate tetrahydrate;

e) stirring until the disappearance of the starting nucleoside by monitoring with TLC;

f) filtering through a pad of celite followed by addition of activated powdered molecular sieves followed by addition of sodium cyanoborohydride and glacial acetic acid dropwise;

g) stirring, filtering through celite and evaporating to dryness and dissolving the residue in ethyl acetate;

h) chromatographically purifying on silica to yield pyrimidine and purine based 7'-TBDPS (Tert-butyl-diphenylsilyl) protected morpholino monomer therefrom;

i) dissolving the compound obtained from step (h) in dry DMF, cooled to 0° C. followed by the addition of triethylamine and trityl chloride and quenching with methanol and obtaining N-trityl, 7'-TBDPS (Tert-butyl-diphenylsilyl) protected morpholino monomer therefrom.

In yet another preferred aspect of the invention there is provided a process for the synthesis of pyrimidine based N-benzyl, 7'-TBDPS (Tert-butyl-diphenylsilyl) protected morpholino monomer; N-phenylalanyl, 7'-TBDPS (Tert-butyl-diphenylsilyl) protected morpholino monomer; N-propargyl, 7'-TBDPS (Tert-butyl-diphenylsilyl) protected morpholino monomer comprises the steps of:

a) Adding imidazole and TBDPSCl dropwise to a stirred solution of the nucleoside in dry DMF under inert atmosphere;

b) stirring and noting the disappearance of the starting material followed by the addition of methanol;

c) stirring and evaporation of the solvent under reduced pressure to yield the 5'-protected nucleoside;

d) dissolving the said 5'-protected nucleoside in methanol by heating on a water bath cooling and
  i) adding sodium meta-periodate and benzylamine for pyrimidine based N-benzyl, 7'-TBDPS (Tert-butyl-diphenylsilyl) protected morpholino monomer;
  ii) adding sodium meta-periodate and propargylamine for N-propargyl, 7'-TBDPS (Tert-butyl-diphenylsilyl) protected morpholino monomer; and
  iii) adding sodium meta-periodate and methyl ester of phenylalanine for N-phenylalanyl, 7'-TBDPS (Tert-butyl-diphenylsilyl) protected morpholino monomer;

e) stirring until the disappearance of the starting nucleoside by monitoring with TLC;

f) filtering through a pad of celite followed by addition of activated powdered molecular sieves followed by addition of sodium cyanoborohydride and glacial acetic acid dropwise;

g) stirring, filtering through celite and evaporating to dryness and dissolving the residue in ethyl acetate;

h) chromatographically purifying on silica to yield pyrimidine based N-benzyl 7'-TBDPS (Tert-butyl-diphenylsilyl) N-phenylalanyl, 7'-TBDPS (Tert-butyl-diphenylsilyl); N-propargyl, 7'-TBDPS (Tert-butyl-diphenylsilyl) protected morpholino monomers therefrom.

In another preferred aspect of the invention there is provided a process for the synthesis of pyrimidine and purine based N-trityl 7'-OH morpholino monomer from pyrimidine and purine based N-trityl, 7'-TBDPS (Tert-butyl-diphenylsilyl) protected morpholino monomers comprising the steps of:

a) adding a solution of 1M TBAF dropwise in a stirred solution of pyrimidine and purine based N-trityl, 7'-TBDPS (Tert-butyl-diphenylsilyl) protected morpholino monomer in dry THF;

b) concentrating and diluting the solution with ethyl acetate followed by purification with silica gel and obtaining the said pyrimidine and purine based N-trityl, 7'-OH morpholino monomer therefrom.

In still another preferred aspect of the invention there is provided a process for the synthesis of pyrimidine based N-benzyl or N-phenylalanyl or N-propargyl 7'-OH morpholino monomer from pyrimidine based N-benzyl or N-phenylalanyl or N-propargyl, 7'-TBDPS (Tert-butyl-diphenylsilyl) protected morpholino monomer comprising the steps of:

a) adding a solution of 1M TBAF dropwise in a stirred solution of pyrimidine based N-benzyl or N-phenylalanyl or N-propargyl, 7'-TBDPS (Tert-butyl-diphenylsilyl) protected morpholino monomer in dry THF;

b) concentrating and diluting the solution with ethyl acetate followed by purification with silica gel and obtaining the said pyrimidine and purine based N-trityl, 7'-OH morpholino monomer therefrom.

In yet another preferred aspect of the invention there is provided a process for the synthesis of purine based N6-Benzoyl 7'-OH N-trityl, morpholino adenosine monomer from N-trityl, 7'-TBDPS (Tert-butyl-diphenylsilyl) protected morpholino adenosine monomer comprising the steps of:

a) co-evaporating N-trityl, 7'-TBDPS (Tert-butyl-diphenylsilyl) protected morpholino adenosine of claim 1 twice with pyridine;

b) adding benzoyl chloride dropwise at 0° C. to the mix of step (a) in dry pyridine and stirring for a period of 15-20 hrs;

c) treating with aqueous ammonia to obtain the mono-protected N6 Benzoyl 7'-TBDPS (Tert-butyl-diphenylsilyl) N-trityl morpholino adenosine;

d) deprotecting the silyl group with 1M TBAF in dry THF to obtain the said N6 Benzoyl-7'-OH N-trityl, morpholino adenosine therefrom.

In another preferred aspect of the invention there is provided a process for the synthesis of purine based N2-Isobutyryl-7'-O-TBDPS-N-trityl morpholino guanosine monomer from N-trityl, 7'-TBDPS (Tort-butyl-diphenylsilyl) protected morpholino guanosine monomer comprising the steps of:

a) stirring a solution of N-trityl, 7'-TBDPS (Tert-butyl-diphenylsilyl) protected morpholino guanosine in dry DMF with isobutyryl anhydride and triethylamine followed by heating;

b) concentrating the mixture obtained of step (a) at reduced pressure followed by chromatographic purification over silica gel and obtaining N2-Isobutyryl-7'-O-TBDPS-N-trityl morpholino guanosine monomer therefrom.

In yet another preferred aspect of the invention there is provided a process for the synthesis of 5-iodo pyrimidine-4'-N-trityl-7'-OH morpholino monomer comprising reacting the pyrimidine based 7'-OH-4'-N-trityl-morpholino monomers with iodochloride in methanol and removing the solvent in vacuo to obtain the said 5-iodo pyrimidine-4'-N-trityl-7'-OH morpholino monomer therefrom.

In still another preferred aspect of the invention there is provided a process for the synthesis of 7'-TBDPS-5-iodo 4'-N-trit-C(N4-Ac)-morpholino monomer comprising the steps of:

a) reacting 7'-TBDPS-C(N4-Ac)-4'-N-free morpholino monomer with $I_2$, iodic acid in $CCl_4$ and HOAc under stirring at room temperature followed by extracting the reaction mixture in dichloromethane;

b) protecting the 4'-N free position of the said morpholino starting material in the presence of trityl chloride, $Et_3N$ and DMF and obtaining the said 7'-TBDPS-5-iodo-4'-N-trit-C(N4-Ac)-morpholino monomer therefrom.

In another aspect of the invention there is provided morpholino monomers involving functionalized 7'-positions including functionalized purine and pyrimidine bases of the type represented hereunder:

(Monomer unit with 7'-$NH_2$)

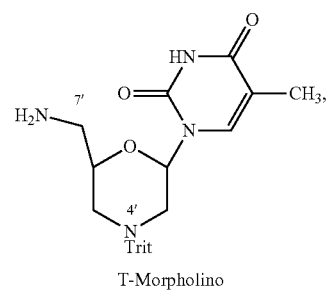

T-Morpholino

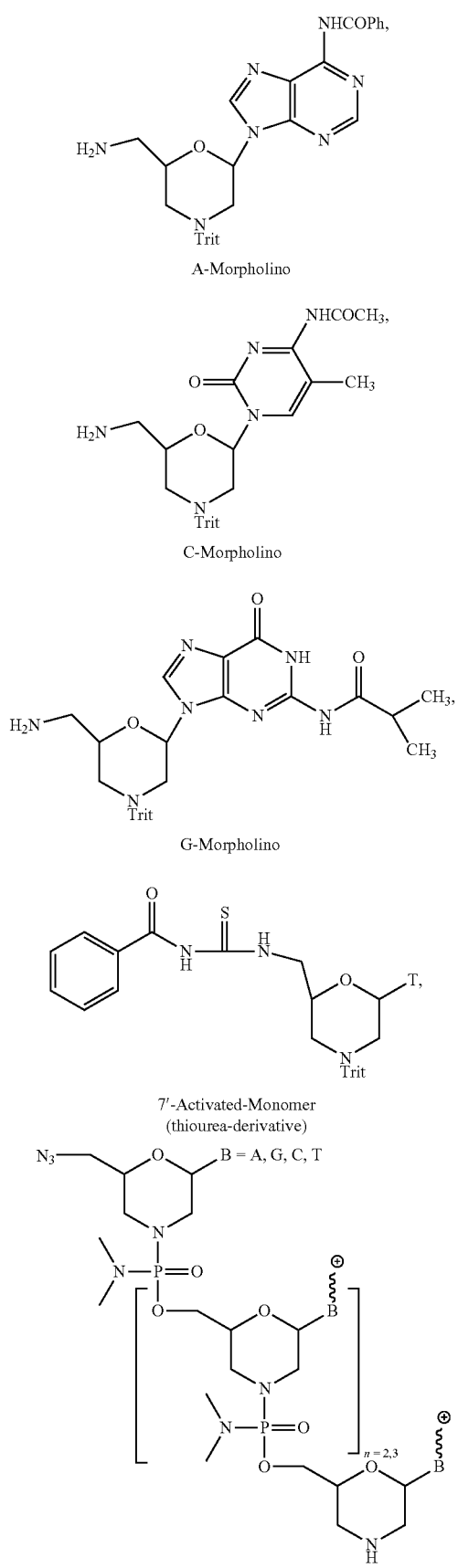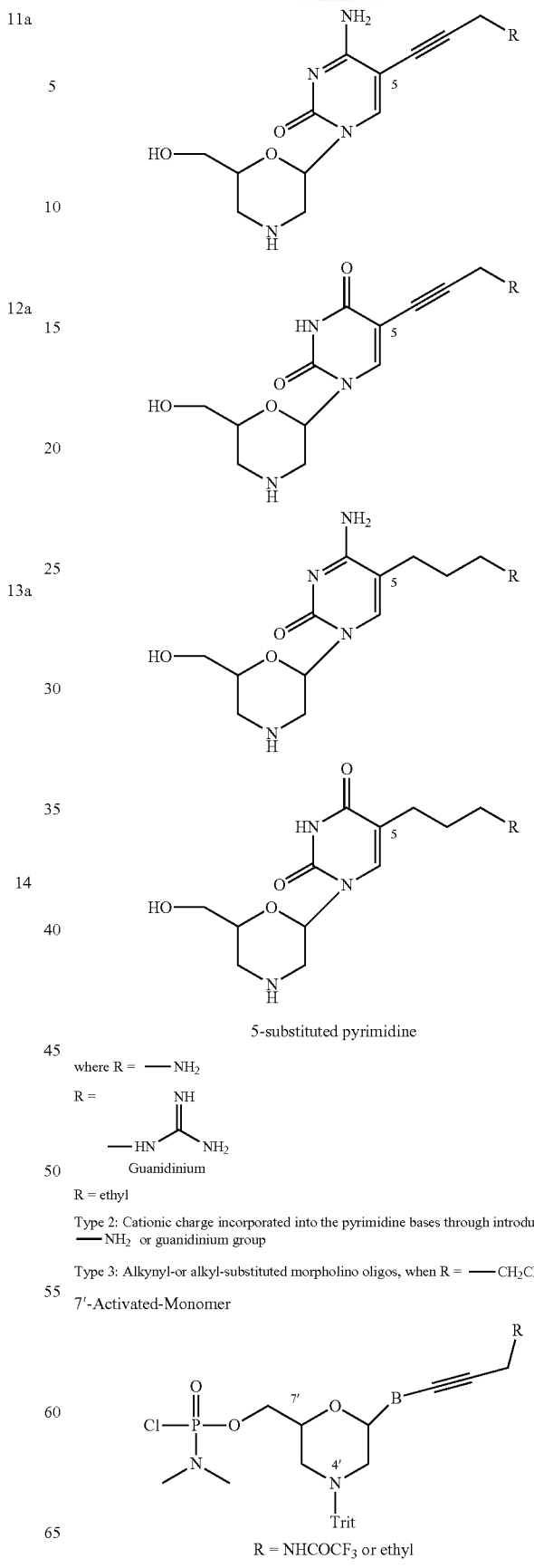

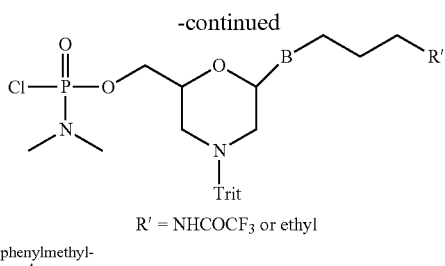

R' = NHCOCF₃ or ethyl

Trit = Triphenylmethyl-
B = U or C(N⁴—Ac)

In another preferred aspect of the invention there is provided morpholino monomers involving functionalized 7'-positions including functionalized purine and pyrimidine bases suitable for oligomers with antisense characteristics.

In still another preferred aspect of the invention there is provided a process for the synthesis of 7'-amino functionalized morpholino monomers comprising the steps of:

a) treating the purine and pyrimidine based 7'-OH N-trityl morpholino precursor monomers with mesylchloride in pyridine;

b) treating the mesylated product obtained from step (a) above with sodium azide in DMF in the presence of ammonium chloride to obtain the azide followed by the reduction of the azide with Pd/C/H₂ and obtaining 7'-amino morpholino monomers therefrom.

In yet another preferred aspect of the invention there is provided a process for the synthesis of thiourea functionalized active purine and pyrimidine based 4'-N-trityl morpholino monomers comprising the steps of:

a) reacting the 7'-amino purine and pyrimidine based N-trityl morpholino precursor monomers in dichloromethane with benzoyl isothiocyanate;

b) evaporating the solvent and purifying by silica gel column to obtain the thiourea derivatized activated monomer therefrom.

Advantageously the said morpholino oligomers suitable for antisense agents and its dye, fluorophore, drug, biomolecule conjugate facilitates its end use in the regulation of gene expression, tissue culture with improved transfection efficiency and related studies on cellular transfection.

The details of the invention, its objects and advantages are explained hereunder in greater detail in relation to non-limiting exemplary illustrations as per the following drawings.

BRIEF DESCRIPTION OF FIGURES

FIG. 18: illustrates the synthesis of 7'-fluorophore-conjugated cationic morpholino.

DETAILED DESCRIPTION OF THE INVENTION

Figure 1:
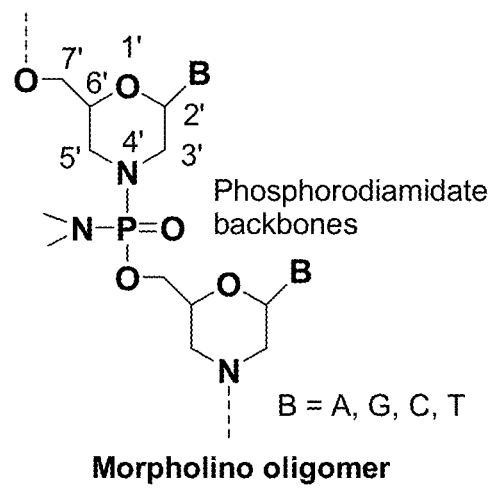
FIG. 1: illustrates phosphorodiamidate backbone of morpholino compound.

As already disclosed herein before, the present invention provides for new variety of morpholino-based antisense agent including partially cationic/completely neutral morpholino-based antisense agents. More specifically the partially cationic based antisense agent comprises of partially modified backbone or incorporation of side-chain-substituted cationic bases while the completely neutral antisense agent comprises of alkynyl and alkyl-substituted bases attached to a conventional morpholino unit to achieve better antisense efficiency and solubility in culture medium. The conventional morpholino based oligomer with phosphorodiamidate linkage is illustrated in FIG. 1.

Figure 2:
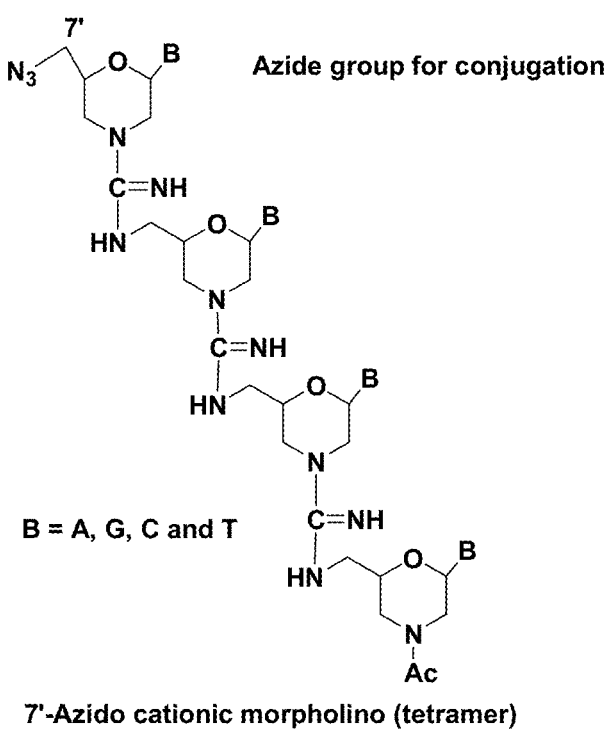
FIG. 2: illustrates the structure of the said cationic morpholino-based antisense agent with modification of phosphorodiamidate backbone by guanidinium linkage with 7'-azido moiety.
Figure 5:
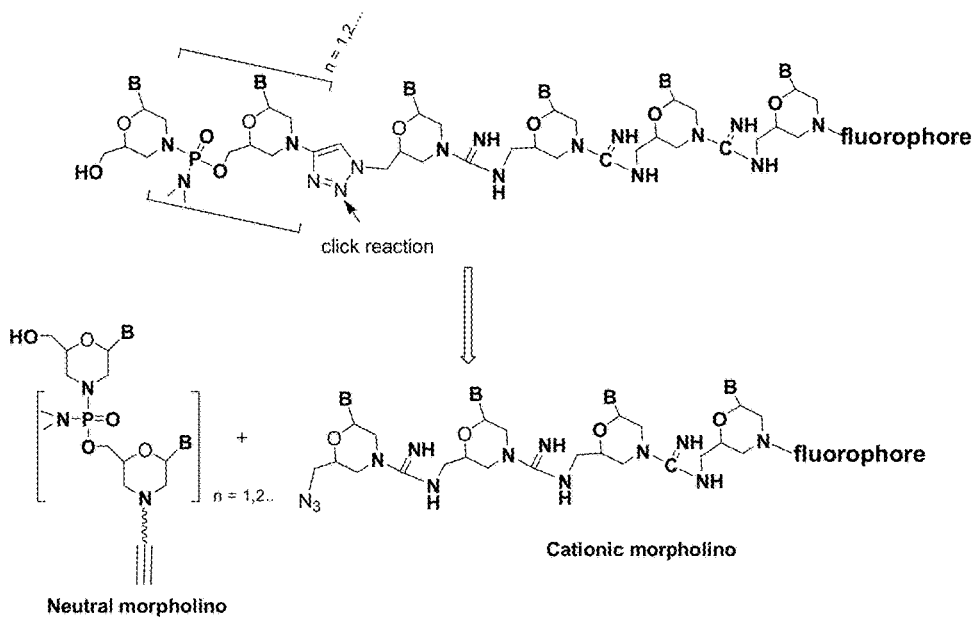
FIG. 5: illustrates the structure of the partially cationic morpholino-oligomer (Type 1) and 4'-conjugated with fluorophore moiety.

Thus in one aspect of the present invention there is provided a Type 1 partially cationic and fully cationic backbone based morpholino oligomer as illustrated in FIGS. 2 and 5 comprising introduction of cationic charge into the morpholino backbone by partially replacing some of the phosphorodiamidate linkage with guanidinium linkage by covalently linking the guanidinium group to morpholino unit wherein the said cationic (positive) charges on the backbone is directed to give rise to cell membrane permeability through electrostatic attraction of the morpholinos to the negatively charged phosphate groups of the cell surface. The agent of the invention does not require to be injected like regular morpholino and just solubilization in culture medium is sufficient for cell penetration. The above Type 1 cationic/partially cationic morpholino oligomers include further modifications by the incorporation of alkynyl and alkyl groups into the purine, pyrimidine bases contained therein.

Figure 6:
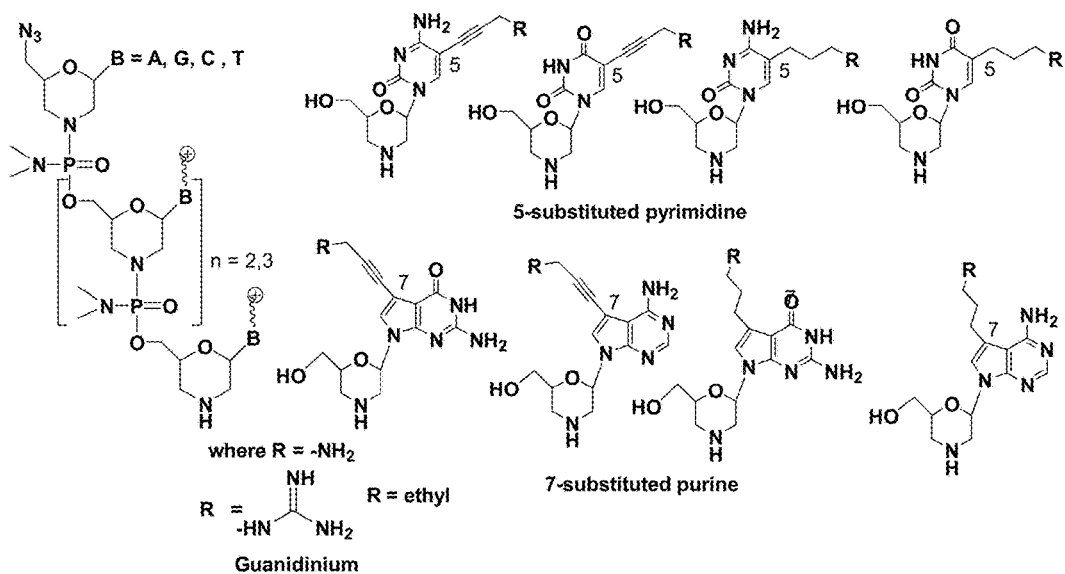
FIG. 6: illustrates the structure of the 7'-azido cationic morpholino-oligomer (Type 2) with modification of pyrimidine and purine bases with guanidinium (R) or amino (R) group at 5- and 7-position, respectively. It includes the alkynyl- or alkyl-substituted pyrimidine bases for better neutral morpholino, when R=CH2CH3.
Figure 7:
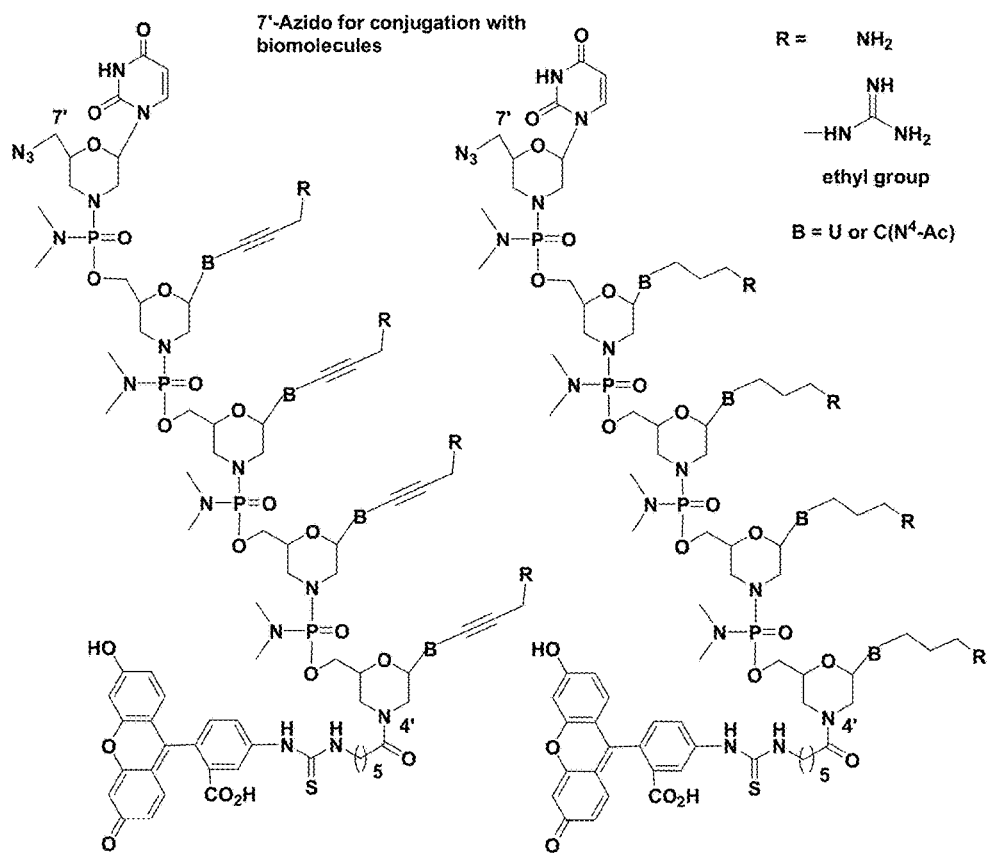
FIG. 7: illustrates the structure of the 7'-azido and 4'-fluorophore-conjugated cationic morpholino-oligomer (Type 2) with the incorporation of cationic charges at 5-position of pyrimidine bases. It includes the 7'-azido and 4'-fluorophore-conjugated neutral morpholino with incorporation of alkynyl- or alkyl-group at 5-position of pyrimidine bases.

In another aspect of the present invention there is provided a Type 2 partially cationic morpholino oligomer comprising cationic charges introduced intermittently through a —NH$_2$ group or a guanidinium group into the purine, pyrimidine bases attached to the conventional morpholino unit of neutral backbone with conventional phosphorodiamidate linkage as illustrated in FIG. 6 and FIG. 7.

In yet another aspect of the present invention there is provided a Type 3 neutral backbone based morpholino oligomer which has total neutral characteristics comprising the incorporation of alkynyl and alkyl groups into the purine, pyrimidine bases attached to the conventional morpholino unit with the phosphorodiamidate backbone for achieving better antisense properties of the said oligomer as illustrated in FIG. 6.

Figure 3:
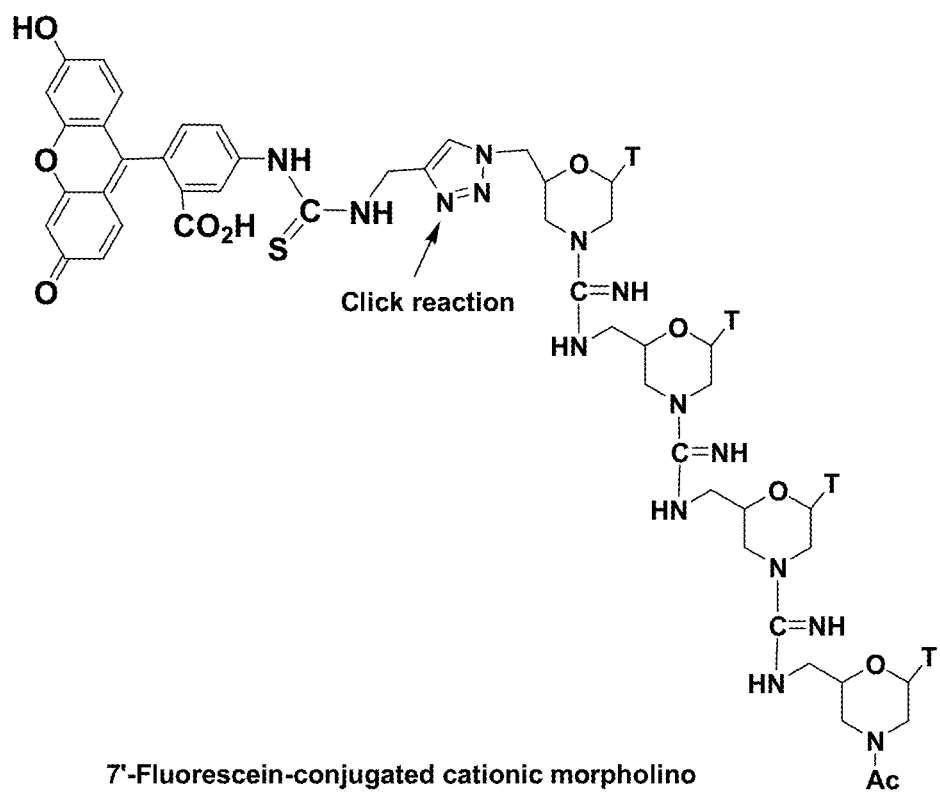
FIG. 3: illustrates the structure of the said cationic morpholino-based antisense agent conjugated with fluorophore at 7'-end via click reaction.
Figure 4:
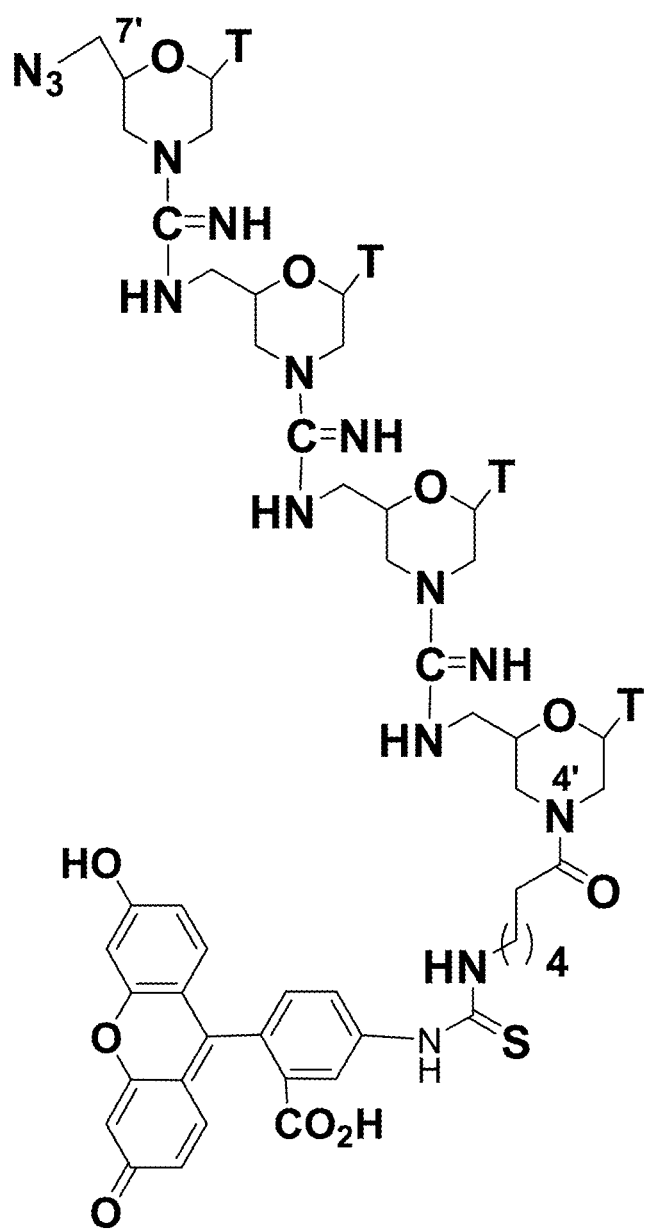
FIG. 4: illustrates the structure of the said cationic morpholino-based antisense agent with 7'-azido and 4'-conjugated fluorophore moiety.

Yet another aspect of the present invention is directed to providing partially cationic morpholino-conjugates of dyes, fluorophore and drug molecules as illustrated in FIGS. 3 and 4 and its method of synthesis to further aid their cellular transfection properties.

In yet further aspect of the present invention there is provided monomers and activated functionalized monomers of the type illustrated in FIGS. 6, 8, 9, 10, 11, 12 and 13 and new synthetic methodology towards the synthesis of morpholino monomers.

In accordance with a basic aspect of the present invention there is provided a method for the synthesis of new and improved partially cationic morpholino based oligomer antisense agent of Type 1 with or without the incorporation of alkynyl and alkyl groups into the purine, pyrimidine bases contained therein.

In accordance with another aspect of the invention there is provided a method for the synthesis of partially cationic morpholino-based antisense agent of Type 2.

In accordance with a further aspect of the invention there is provided a method for the synthesis of the new and improved completely neutral morpholino oligomers of Type 3 that includes the 5-alkynyl- or 5-alkyl-substitution pyrimidines.

In accordance with a preferred aspect of the invention there is provided a synthetic method for the synthesis of cationic morpholino-conjugates of dyes, fluorophore and drug to further aid in the cellular transfection properties of the said antisense agents.

Advantageously enough, the present invention also features a new synthetic methodology for the synthesis of morpholino monomers.

Advantageously, the said synthetic method of the present invention for the synthesis of improved morpholino-based oligomers facilitates the antisense properties of the said oligomers in-vivo involving zebrafish embryos that might facilitate the inhibition of several endogenous zebrafish genes.

In another embodiment of the present invention, the method of synthesizing the partially cationic morpholino based antisense agent comprises the steps of substitution with guanidinium or free amino groups at 5- or 7-position of pyrimidine or purine bases respectively.

The said cationic antisense agent solves the long standing problem of transfection associated with neutral morpholinos in tissue culture and aides the cellular transfection of cationic morpholino in conjugation with dye, fluorophore, drugs.

Advantageously, the solubilization of the said antisense agent of the present invention in culture medium such as in embryo culture medium might be sufficient for embryo penetration and discards the need to be injected like regular morpholino.

In yet another embodiment of the present invention, the synthetic methodology of the present invention leading to the modification achieved through the base substitution reaction does not affect the Watson-Crick base pairing, thus resulting in more specific gene regulation.

Figure 14:
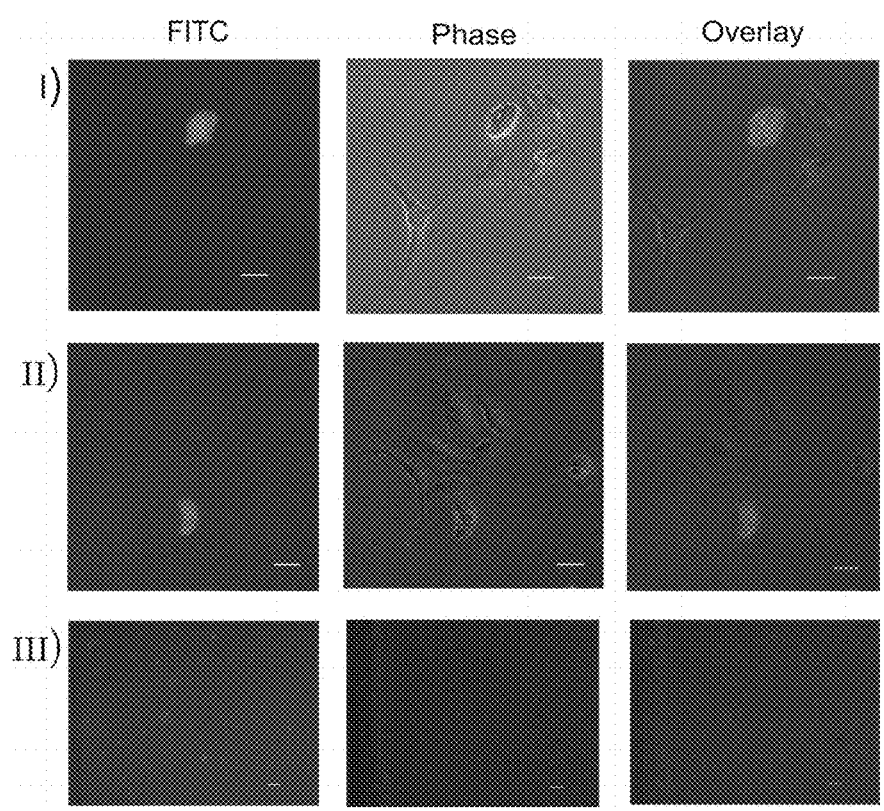
FIG. 14: Microscopy images of HeLa cells cultured in the presence of Morpholino 20 (1500 nM concentration); I), II) & III) represents images of different sections of the cells; Bar represents 50 μm.

More specifically, it is possible to synthesize the antisense agent involving the simple step of incorporating guanidinium group directly to the morpholino oligos to make partially cationic morpholinos (FIG. 2) as compared to the neutral morpholino oligos (FIG. 1) that binds more strongly with DNA or RNA because of their positive charge. The above process of the invention discards the need to conjugate morpholino with peptide separately. The said cationic antisense agent is found to solve the long standing problem of transfection associated with neutral morpholinos in tissue culture as the same did not require to be injected like regular morpholinos and just solubilization in culture medium was sufficient for penetration of the said new morpholinos into the cells. FIG. 14 illustrates the microscopy images of HeLa cells cultured in the presence of fluorophore-conjugated cationic morpholino that goes to prove that it is sufficient for cellular transfection.

It was thus possible by way of the invention to provide for new synthetic method by which the cationic charges could be added partially to the morpholino oligos by replacing some of the phosphorodiamidate linkages to guanidinium linkages. In another embodiment of the present invention, the said cationic morpholino-based antisense agent is also alternatively prepared by the incorporation of the guanidinium group at 5- or 7-position of pyrimidine or purine bases attached to the morpholino unit respectively through substitution reaction without the modification of the backbone in this instance and by such modifications Watson-Crick base pair is not affected.

Type 1: Introduction of cationic charge to the morpholino backbone:
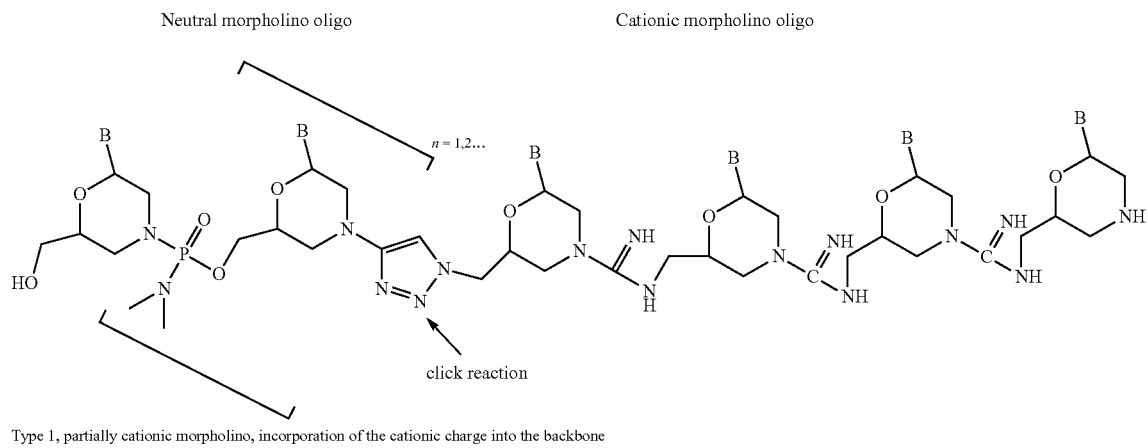
Type 1, partially cationic morpholino, incorporation of the cationic charge into the backbone
Type 2: Introduction of cationic charge to the purine, pyrimidine bases:
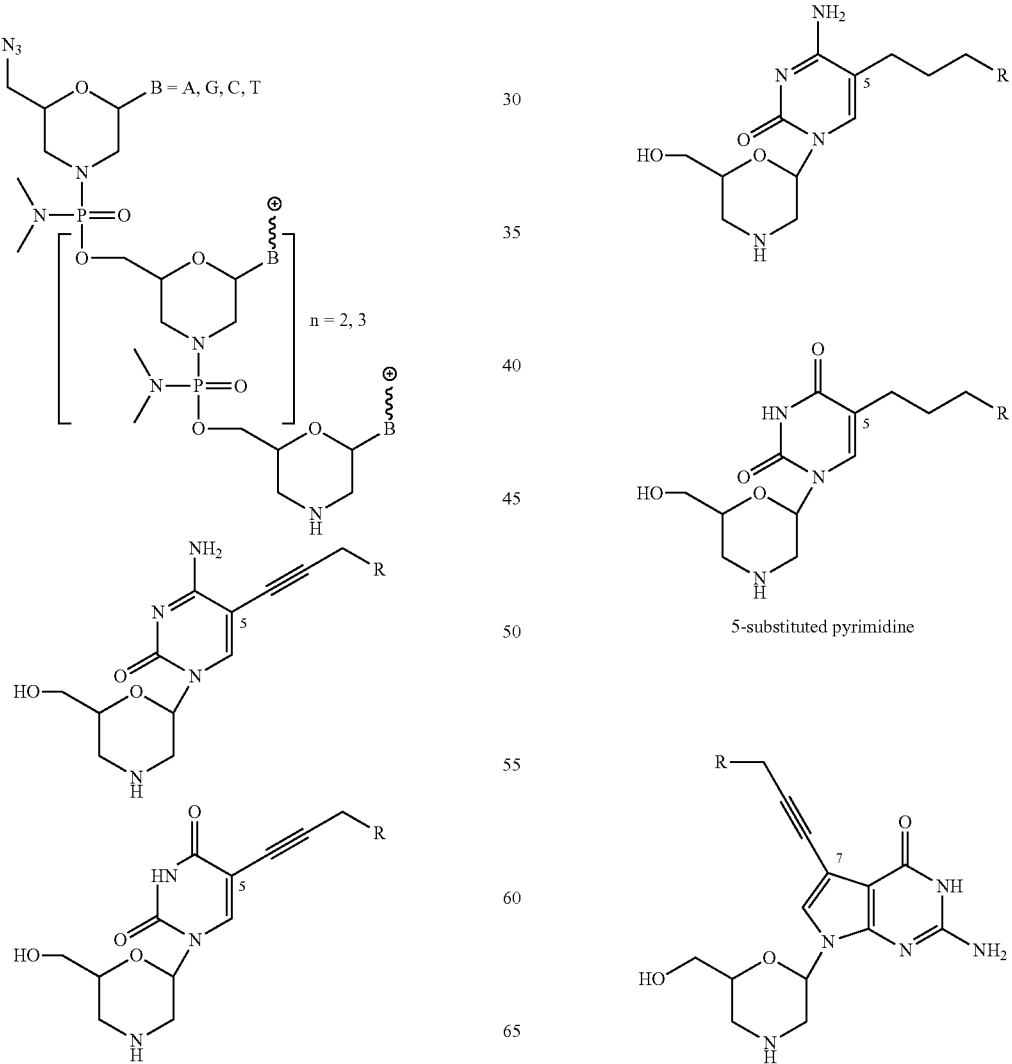
5-substituted pyrimidine -continued

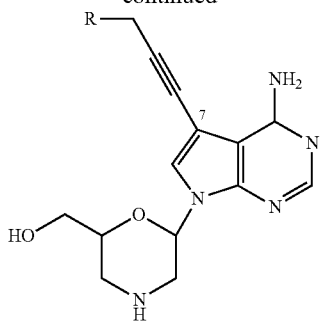

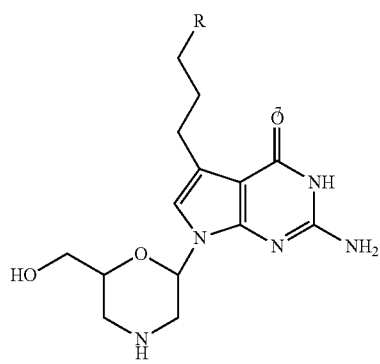

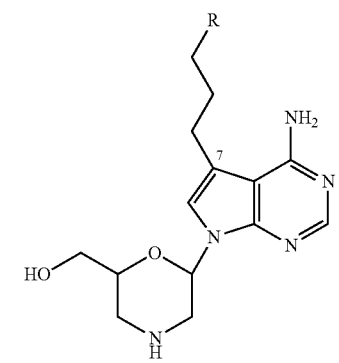

7-substituted purine where R = —NH₂

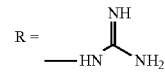

Guanidinium
R = ethyl

Type 2: Cationic charge incorporated into the pyrimidine bases through introduction by —NH₂ or guanidinium group at 5-position.
Type 3: Alkynyl- or alkyl- substituted morpholino oligos, when R = —CH₂CH₃

The positive charges of the backbone give rise to cell membrane permeability through electrostatic attraction of the morpholinos to the negatively charged phosphate groups of the cell surface. These agent does not need injection like regular morpholino, just solubilization in embryo culture medium may be sufficient for embryo penetration.

The following examples are discussed by the way of illustration to the present invention and should not be construed to limit the scope of the present invention.

EXAMPLE 1

Figure 8:
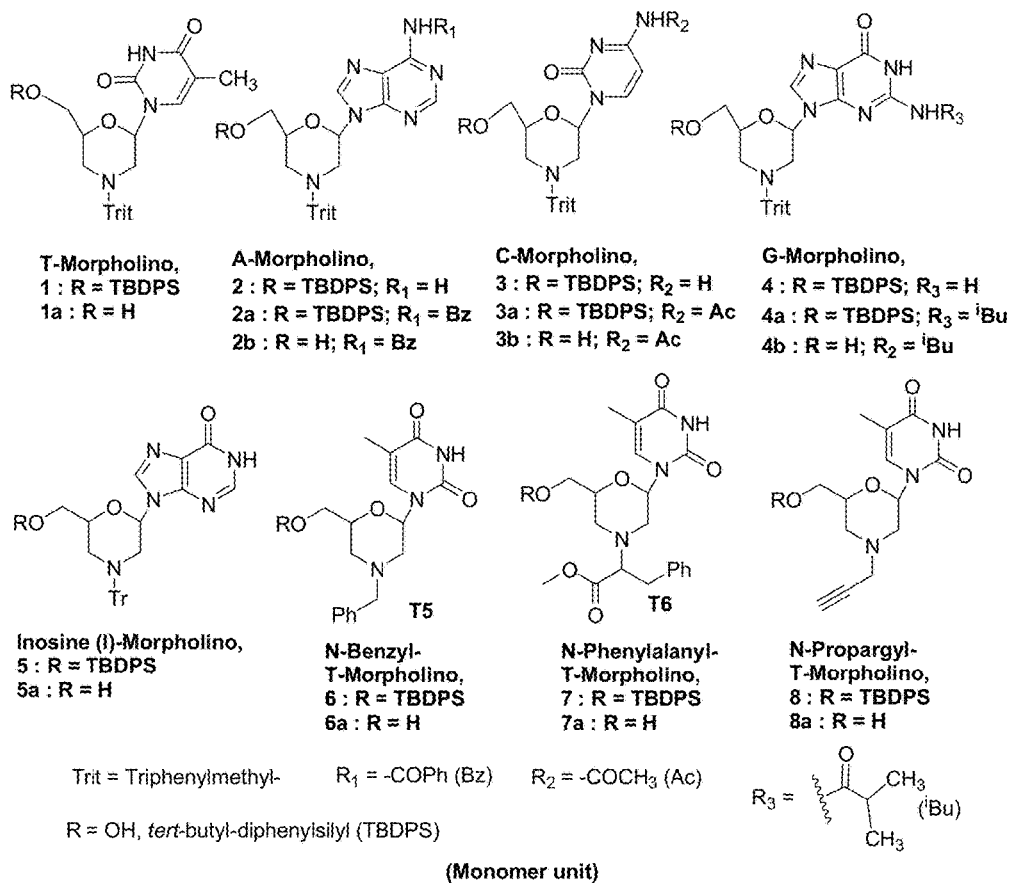
FIG. 8: illustrates the morpholino monomers.
Figure 15:
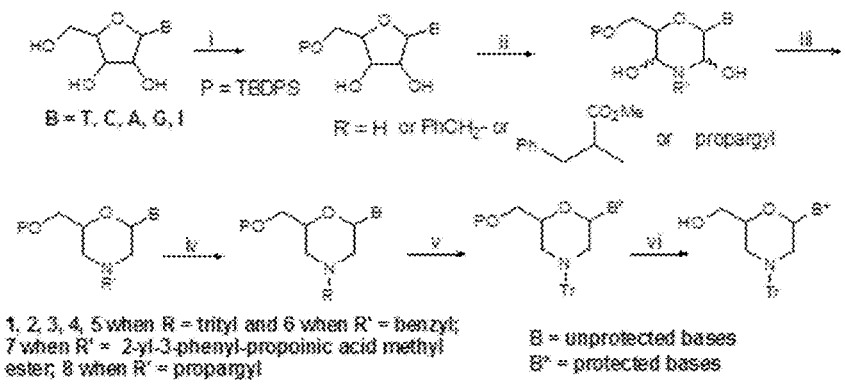
FIG. 15: illustrates the synthesis of morpholino monomers.

Synthesis of Morpholino Monomers 1, 2, 3, 4, 5, 6, 7 and 8 in FIG. 8 (FIG. 15)

The synthetic route is different from the previously reported (U.S. Pat. No. 5,185,444, *Gene Tools LLC and Nature Chemical Biology.* 2007, 3, 650 by Chen et. al.).

The unprotected ribonucleosides (A, G, C, T & I) were first converted to the 5'OTBDPS (tert-butyl-diphenylsilyl-) protected nucleosides and then used for morpholino synthesis.

7'-O-TBDPS-N-trityl morpholino thymine (1)

To a stirred solution of 5-methyl uridine (7.75 mmol) in dry DMF (8 ml) were added imidazole (19.33 mmol) and TBDPSCI (9.79 mmol) dropwise under Ar. The mixture was stirred at room temperature for 4 h. After the disappearance of the starting material (TLC), 2 ml of MeOH was added to the mixture, and was stirred at room temperature for 10 min. The solvent was removed in reduced pressure. The residue was dissolved in EtOAc (50 ml) and washed thoroughly with water (20 ml×3) and brine (20 ml). This was dried over $Na_2SO_4$ and concentrated under reduced pressure to give the crude product which upon trituration with ether obtained the product as white solid (3.57 g, 93%) along with 3-4% of the di-protected nucleoside (*Tetrahedron* 1998, 54, 11151 by Magdalena Endovl et. al.). This was used in the next step without further purification.

The 5' protected nucleoside (above) (5.03 mmol) was dissolved in 40 ml of methanol by slight heating in water bath. It was cooled to room temperature and were added sodium meta-periodate (5.54 mmol), ammonium biborate tetrahydrate (6.53 mmol). The reaction mixture was stirred at room temperature for two hours when the starting material was consumed and an envelope of very closely spaced ninhydrin active spots was generated. The reaction mixture was filtered through a pad of celite and were added activated powdered 4 Å molecular sieves (1.51 g, 300 mg/mmol) followed by sodium cyanoborohydride (10.06 mmol) and glacial acetic acid (10.06 mmol) dropwise. The reaction mixture was stirred for another 2.5 hours when the intermediate product was completely reduced. This was again filtered through celite and evaporated to dryness. The residue was dissolved in EtOAc (50 ml) and washed with water (15 ml×2) and brine (25 ml). The solvent was dried and removed under reduced pressure. Chromatographic purification ($SiO_2$, elution with 1-5% methanol in $CH_2Cl_2$) afforded 1.12 g (overall 45% yield from 5-methyl uridine) of the title compound as a white solid. Alternatively this crude can be used in the next step without purification.

The above morpholino (1.88 mmol) was dissolved in dry dimethylformamide (6 ml) and cooled to 0° C. Triethylamine (3.95 mmol) was added to this followed by trityl chloride (2.06 mmol) portion wise. After one hour the reaction was quenched with methanol and concentrated in reduced pressure. This was diluted with EtOAc (50 ml) and washed with water (20 ml×3) and brine (30 ml). Solvent was removed in vacuo, and the residue was purified by triethylamine treated $SiO_2$ column chromatography (0-2% MeOH/$CH_2Cl_2$) to give the product 1 as a white solid (1.2 g, 89%).

$^1$H NMR (500 MHz, CDCl₃): δ0.88 (s, 9H), 1.28 (t, 1H, J=10.0 Hz), 1.44 (t, 1H, J=11.0 Hz), 1.67 (s, 3H), 3.18 (d, 1H, J=12.0 Hz), 3.24 (dd, 1H, J=11.5, 2.0 Hz), 3.52 (dd, 1H,

J=10.8, 5.8 Hz), 3.65 (dd, 1H, J=10.8, 4.3 Hz), 4.15-4.18 (m, 1H), 6.01 (dd, 1H, J=9.3, 2.3 Hz), 6.85 (s, 1H), 7.11-7.50 (m, 25H), 7.95 (br s, 1H);

$^{13}$C NMR (75 MHz, CDCl$_3$): δ 12.4, 19.2, 26.7, 49.8, 52.1, 64.5, 76.8, 77.1, 80.5, 110.3, 126.5, 127.7, 127.9, 129.2, 129.7, 129.8, 133.1, 133.3, 135.5, 135.5, 135.6, 149.8, 163.6;

IR (KBr): v 3188, 3034, 2930, 1692, 1464, 1265, 1109, 708 cm$^{-1}$.

HRMS (ESI) calcd for C$_{45}$H$_{47}$N$_3$O$_4$SiNa (M+Na) 744.3234, found 744.3233.

7'-OH—N-trityl morpholino thymine (1a)

To a stirred solution of 1 (above) (1.11 mmol) in dry THF was added dropwise a solution of 1 M TBAF in THF (2.22 ml, 2.22 mmol) and stirred for 1.5 h at room temperature. The reaction mixture was concentrated and diluted with EtOAc (45 ml), washed with water (2×20 ml) and brine (30 ml), dried (Na$_2$SO$_4$), concentrated and purified over silica gel (20% EtOAc in petroleum ether and then 5% MeOH in DCM) to afford a white solid 1a (507 mg, 97%) (FIG. 15).

$^1$H NMR (300 MHz, CDCl$_3$): δ 1.34 (t, 2H, J=10.8 Hz), 1.70 (s, 3H), 1.93 (br s, 1H), 2.97 (d, 1H, J=11.9 Hz), 3.22 (d, 1H, J=11.2 Hz), 3.49 (br s, 2H), 4.16 (br s, 1H), 6.05 (d, 1H, J=9.6 Hz), 6.88 (s, 1H), 7.08 (d, 3H, J=6.8 Hz), 7.18 (m, 6H), 7.34 (br s, 6H), 8.42 (br s, 1H);

$^{13}$C NMR (75 MHz, CDCl$_3$): δ 12.5, 48.9, 52.1, 63.8, 76.9, 77.8, 80.6, 110.7, 126.7, 128.1, 129.3, 135.6, 149.8, 163.5;

IR (KBr): v 3410, 3190, 3057, 2885, 1692, 1447, 1265, 1105, 712 cm$^{-1}$.

HRMS (ESI) calcd for C$_{29}$H$_{29}$N$_3$O$_4$Na (M+Na)$^+$ 506.2056, found 506.2059.

7'-O-TBDPS-N-trityl morpholino adenosine (2)

5'-OH of adenosine was protected with TBDPS group according to the procedure reported in *Helv chim acta* 2003, 86, 703 by Lei Zhang et. al. and obtained 97% yield.

Morpholino synthesis was done according to the procedure mentioned for 1.

$^1$H NMR (500 MHz, CDCl$_3$) δ 0.94 (s, 9H), 1.59 (t, 1H, J=11.0 Hz), 1.59, (t, 1H, J=10.5 Hz), 3.34 (d, 1H, J=12.0 Hz), 3.41 (d, 1H, J=11.5 Hz), 3.58 (dd, 1H, J=11.0, 6.0 Hz), 3.75 (dd, 1H, J=9.8, 4.3 Hz), 4.32-4.34 (m, 1H), 5.91-5.96 (m, 2H), 6.30 (d, 1H, J=9.5 Hz), 7.18 (t, 3H, J=6.8 Hz), 7.26-7.56 (m, 22H), 7.62 (s, 1H), 8.35 (s, 1H);

$^{13}$C NMR (125 MHz, CDCl$_3$): δ 19.3, 26.8, 50.0, 53.3, 64.6, 77.0, 77.1, 79.9, 119.2, 126.5, 127.7, 127.9, 129.3, 129.7, 129.8, 133.2, 133.4, 135.6, 138.1, 149.4, 153.3, 155.5;

IR (KBr): v 3327, 3055, 2928, 1676, 1636, 1595, 1471, 1105, 709 cm$^{-1}$.

HRMS (ESI) calcd for C$_{45}$H$_{46}$N$_6$O$_2$SiNa (M+Na)$^+$ 753.3349, found 753.3347.

N6-Benzoyl-7'-O-TBDPS-N-trityl morpholino adenosine (2a)

The compound 2 (150 mg, 0.21 mmol) was co-evaporated with pyridine twice. To a stirred solution of this in dry pyridine (3 ml) at 0° C. was added benzoyl chloride (0.12 ml, 0.96 mmol) dropwise. After 18 hours of stirring at room temperature, the diprotection was found to be completed. The mixture was again cooled to 0° C. and 0.5 ml of 30% aqueous ammonia was added and the mixture was stirred at this temperature for 1 h 45 min. The reaction mixture was then evaporated to near dryness and the residue was dissolved in 25 ml of chloroform. This solution was washed with saturated NaHCO$_3$ (15 ml) and then with saturated NaCl (15 ml), dried over Na$_2$SO$_4$, and evaporated to dryness. The residue was purified by column chromatography using 0-2% MeOH in CH$_2$Cl$_2$ as the eluant to produce 2a as a white solid (133 mg) (FIG. 15).

N6-Benzoyl-7'-OH—N-trityl morpholino adenosine (2b)

Silyl deprotection from 2a (100 mg, 0.119 mmol) with 1M TBAF in THF (238 μL, 0.238 mmol) for 2 h furnished the product 2b as a white solid (59.6 mg, 85%) (FIG. 15).

$^1$H NMR (500 MHz, CDCl$_3$) δ 1.53 (t, 1H, J=11.3 Hz), 1.74 (t, 1H, J=10.8 Hz), 3.05 (d, 1H, J=12.0 Hz), 3.29 (br s, 1H), 3.42 (d, 1H, J=11.5 Hz), 3.46-3.55 (m, 2H), 4.24-4.26 (m, 1H), 6.29 (d, 1H, J=9.5 Hz), 7.11 (t, 3H, J=7 Hz), 7.22 (t, 7H J=7.5 Hz), 7.40-7.44 (m, 8H), 7.51 (t, 1H, J=7.3 Hz), 7.81 (s, 1H), 7.96 (d, 2H, J=7.0 Hz), 8.71 (s, 1H), 9.38 (br s, 1H);

$^{13}$C NMR (125 MHz, CDCl$_3$):
δ 48.9, 53.1, 63.5, 76.9, 77.6, 80.4, 122.4, 126.7, 128.0, 128.03, 128.8, 129.2, 132.7, 133.8, 140.3, 149.6, 151.1, 152.9, 164.9;

IR (KBr): v 3404, 3057, 2886, 1691, 1608, 1450, 1251, 1103, 712 cm$^{-1}$.

HRMS (ESI) calcd for C$_{36}$H$_{32}$N$_6$O$_3$SiNa (M+Na)$^+$ 619.2434, found 619.2432.

7'-O-TBDPS-N-trityl morpholino cytidine (3)

5'-OH of cytosine was protected with TBDPS group according to the procedure reported in *Can. J. Chem.* 1975, 53, 2975 by Stephenh Anessia et. al. and obtained in 94% yield.

Morpholino synthesis was done according to the procedure mentioned for 1.

$^1$H NMR (500 MHz, CDCl$_3$): δ 0.87 (s, 9H), 1.11 (t, 1H, J=10.3 Hz), 1.38 (t, 1H, J=11.0 Hz), 3.17 (d, 1H, J=11.5 Hz), 3.31 (d, 1H, J=11.0 Hz), 3.48 (dd, 1H, J=10.5, 6.0 Hz), 3.65 (dd, 1H, J=10.5, 4.5 Hz), 4.13-4.15 (m, 1H), 5.42 (d, 1H, J=7.0 Hz), 6.09 (dd, 1H, J=7.0, 1.5 Hz), 7.01 (d, 1H, J=7.0 Hz), 7.07-7.44 (m, 24H), 7.49 (d, 2H, J=7.0 Hz), 7.95 (s, 1H).

$^{13}$C NMR (125 MHz, CDCl$_3$): δ 19.2, 26.7, 50.0, 52.8, 64.7, 76.8, 76.9, 81.4, 93.8, 126.3, 126.9, 127.2, 127.6, 127.7, 127.8, 127.9, 128.0, 128.8, 129.3, 129.6, 129.8, 133.1, 133.5, 135.5, 135.55, 141.2, 155.1, 162.5, 165.5;

IR (KBr): v 3333, 3068, 2930, 2857, 1645, 1489, 1109, 706 cm$^{-1}$.

HRMS (ESI) calcd for C$_{44}$H$_{46}$N$_4$O$_3$SiNa (M+Na)$^+$ 729.3237, found 729.3239.

N4-Acetyl-7'-O-TBDPS-N-trityl morpholino cytidine (3a)

To a stirred solution of 3 (200 mg, 0.28 mmol) in dry THF (5 ml) were added Et$_3$N (0.18 ml, 1.29 mmol) and acetic anhydride (60 μL, 0.65 mmol) drop wise at 0° C. After stirring at room temperature for overnight, the solvent was evaporated at reduced pressure. Usual work up and chromatographic purification (0-2.5% MeOH in DCM) afforded the product as a white solid (170 mg, 80%) (FIG. 15).

N4-Acetyl-7'-OH—N-trityl morpholino cytidine (3b)

Silyl deprotection 3a was done by 1M TBAF and yield was 75% (FIG. 15).

$^1$H NMR (500 MHz, CDCl$_3$): δ 1.24-1.29 (m, 1H), 1.47 (t, 1H, J=11.3 Hz), 1.93 (br s, 1H), 2.20 (s, 3H), 3.10 (dd, 1H, J=10.5, 2.0 Hz), 3.50 (dd, 1H, J=8.3, 2.3 Hz), 3.59-3.63 (m, 2H), 4.29-4.32 (m, 1H), 6.28 (dd, 1H, J=9.0, 2.0 Hz), 7.17 (t, 3H, J=7.0 Hz), 7.26-7.30 (m, 8H), 7.46 (br s, 5H), 7.62 (d, 1H, J=7.5 Hz), 8.80 (br s, 1H);

$^{13}$C NMR (125 MHz, CDCl$_3$): δ 25.0, 49.1, 53.0, 63.8, 77.0, 78.0, 82.2, 96.7, 126.6, 128.0, 128.1, 129.3, 130.0, 144.5, 154.5, 162.7;

IR (KBr): ν 3424, 3244, 2926, 1720, 1657, 1560, 1491, 1312, 709 cm$^{-1}$.

HRMS (ESI) calcd for C$_{30}$H$_{30}$N$_4$O$_4$SiNa (M+Na)$^+$ 533.2165, found 533.2165.

7'-O-TBDPS-N-trityl morpholino guanosine (4)

5'-OH of guanosine was protected with TBDPS group according to the procedure reported in *Bioorg. Med. Chem.* 1993, 1, 369 by Scott A. Van Arman et. al. and obtained in 95% yield.

Morpholino synthesis was done according to the procedure mentioned for 1.

$^1$H NMR (500 MHz, CDCl$_3$) δ 0.87 (s, 9H), 1.47 (t, 1H, J=10.5 Hz), 1.57 (t, 1H, J=10.5 Hz), 3.23 (d, 1H, J 11.0 Hz), 3.32 (d, 1H, J=11.0 Hz), 3.50 (dd, 1H, J=10.5, 6.0 Hz), 3.68 (dd, 1H, J=10.5, 4.0 Hz), 4.21-4.22 (m, 1H), 5.94 (d, 1H, J=9.5 Hz), 6.17 (br s, 2H), 7.05-7.57 (m, 26H), 11.80 (br s, 1H);

$^{13}$C NMR (125 MHz, CDCl$_3$): δ 18.2, 25.9, 49.0, 52.0, 63.6, 75.9, 79.2, 117.0, 125.5, 126.6, 126.7, 126.8, 127.0, 128.3, 128.66, 128.72, 128.9, 132.2, 132.3, 134.0, 134.3, 134.4, 134.5, 150.0, 152.6, 158.1;

IR (KBr): ν 3331, 3066, 2929, 1692, 1626, 1361, 1109, 704 cm$^{-1}$.

HRMS (ESI) calcd for C$_{45}$H$_{46}$N$_6$O$_3$SiNa (M+Na)$^+$ 769.3298, found 769.3297.

N2-Isobutyryl-7'-O-TBDPS-N-trityl morpholino guanosine (4a)

To a stirred solution 4 (100 mg, 0.134 mmol) in dry DMF were added isobutyryl anhydride (44 μL, 0.268 mmol) and triethylamine (56 μL, 0.402 mmol). After heating at 140° C. for 3 h, another batch of isobutyryl anhydride (44 μL, 0.268 mmol) and triethylamine (75 μL, 0.536 mmol) was added and again heated for 2 h. The mixture was concentrated at reduced pressure, diluted with chloroform (25 ml), washed with water (3×10 ml), saturated NaHCO$_3$ (10 ml) and then with saturated NaCl (15 ml). This was dried over Na$_2$SO$_4$, and evaporated to dryness. Chromatographic purification (SiO$_2$, 0-2% MeOH in DCM) furnished a solid, yellowish white product 4a in 71% yield (FIG. 15).

N2-Isobutyryl-7'-OH—N-trityl morpholino guanosine (4b)

The fully morpholino nucleoside 4a was reacted with 1M TBAF in THF to obtain the product 4b as a white solid in 94% yield (FIG. 15).

$^1$H NMR (500 MHz, CDCl$_3$): δ 1.26 (d, 6H, J=7.0 Hz) 1.52 (t, 1H, J=11.0 Hz), 1.78 (t, 1H, J=10.5 Hz), 2.73 (sept, 1H, J=6.8 Hz), 3.10 (d, 1H, J=12.0 Hz), 3.35 (d, 1H, J=12.0 Hz), 3.53-3.60 (m, 2H), 4.27-4.30 (m, 1H), 5.97 (dd, 1H, J=10.0, 2 Hz), 7.16 (m, 3H), 7.26-7.51 (m, 13H);

$^{13}$C NMR (125 MHz, CDCl$_3$): δ 18.9, 19.2, 36.5, 48.9, 52.5, 63.6, 77.0, 77.8, 80.6, 120.8, 126.7, 128.0, 129.4, 136.5, 147.8, 155.8, 177.8.

IR (KBr): □□3408, 3186, 2972, 1682, 1607, 1406, 1024, 712 cm$^{-1}$.

HRMS (ESI) calcd for C$_{33}$H$_{34}$N$_6$O$_4$Na (M+Na)$^+$ 601.2539, found 601.2535.

7'-O-TBDPS-N-trityl morpholino inosine (5)

The 5'-OH of inosine was protected with TBDPS group according to the following procedure.

To a suspension of inosine (750 mg, 2.79 mmol) and imidazole (470 mg, 6.98 mmol) in DMF (8 ml) was added TBDPSCl dropwise under Ar. The mixture was stirred for 6 h when a clear solution was obtained. The reaction was quenched with methanol and solvent was evaporated off. This was diluted with chloroform (60 ml), washed with water and brine, dried and concentrated to obtain the product as a white solid (1.38 g, 98%). This was used in the next step without further purification.

Morpholino synthesis was done according to the procedure mentioned for 1.

$^1$H NMR (500 MHz, CDCl$_3$) δ 0.97 (s, 9H), 1.61 (t, 1H, J=11.3 Hz), 1.74 (t, 1H, J=10.5 Hz), 3.34 (d, 1H, J=12.0 Hz), 3.42 (d, 1H, J=11.0 Hz), 3.61 (dd, 1H, J=10.8, 5.7 Hz), 3.77 (dd, 1H, J=10.8, 4.7 Hz), 4.32-4.34 (m, 1H), 6.25 (dd, 1H, J=10.0, 2.0 Hz), 7.19-7.58 (m, 25H), 7.66 (s, 1H), 8.23 (s, 1H).

$^{13}$C NMR (125 MHz, CDCl$_3$): δ 19.2, 26.8, 49.9, 53.4, 64.6, 76.9, 77.2, 80.3, 126.6, 127.7, 127.9, 129.2, 129.7, 129.8, 133.3, 135.5, 137.8, 148.3, 159.3.

IR (KBr): ν 3055, 2876, 1699, 1587, 1510, 1109, 708 cm$^{-1}$.

HRMS (ESI) calcd for C$_{45}$H$_{45}$N$_5$O$_3$SiNa (M+Na)$^+$ 754.3189, found 754.3188.

7'-OH—N-trityl morpholino inosine (5a)

TBDPS was deprotected with 1M TBAF and yield was 81% (FIG. 15).

$^1$H NMR (500 MHz, CDCl$_3$) δ 1.61 (t, 1H, J=11.3 Hz), 1.85 (t, 1H, J=10.5 Hz), 3.16 (d, 1H, J=11.5 Hz), 3.43 (d, 1H, J=11.0 Hz), 3.59 (dd, 1H, J=12.0, 6.0 Hz), 3.65 (dd, 1H, J=10.3, 3.8 Hz), 4.33-4.37 (m, 1H), 6.27 (dd, 1H, J=10.0, 2.0 Hz), 7.19 (t, 3H, J=7.3 Hz), 7.30 (t, 6H, J=7.5 Hz), 7.48 (m, 6H), 7.78 (s, 1H), 8.07 (s, 1H);

$^{13}$C NMR (125 MHz, DMSO-d$_6$):
δ 50.0, 525, 62.4, 76.9, 77.2, 80.4, 124.5, 126.9, 128.4, 129.4, 138.4, 146.5, 148.0, 157.0.

IR (KBr): ν 3385, 3084, 2874, 1694, 1587, 1213, 709 cm$^{-1}$.

HRMS (ESI) calcd for C$_{29}$H$_{27}$N$_5$O$_3$Na (M+Na)$^+$ 516.2012, found 516.2012.

7'-O-TBDPS-N-benzylmorpholino thymine (6), 7'-O-TBDPS-N-(phenylalanine methyl ester)morpholino thymine (7) and 7'-O-TBDPS-N-propargyl-morpholino thymine (8)

These compounds were synthesized according to the procedure mentioned for 1 and amines were used such as benzylamine, methyl ester phenyl alanine and propargyl amine, respectively instead of ammonium biborate (FIG. 15).

7'-O-TBDPS-N-benzylmorpholino thymine (6)

Overall yield 62% from starting material.

$^1$H NMR (500 MHz, CDCl$_3$): δ 1.03 (s, 9H), 1.87 (s, 3H), 1.97 (t, 1H, J=10.3 Hz), 2.05 (t, 1H, J=11.0 Hz), 2.87 (d, 1H, J=11.5 Hz), 2.97 (d, 1H, J=10.5 Hz), 3.58 (dd, 2H, J=20.3, 13.3 Hz), 3.69 (dd, 1H, J=11.0, 5.0 Hz), 3.74 (dd, 1H, J=11.0, 4.5 Hz), 3.93-3.95 (m, 1H), 5.82 (dd, 1H, J=9.8, 2.8 Hz), 7.20 (s, 1H), 7.27-7.37 (m, 9H), 7.40-7.45 (m, 4H), 7.61-7.64 (m, 4H), 7.95 (br s, 1H);

$^{13}$C NMR (75 MHz, CDCl$_3$): δ 12.6, 19.4, 26.9, 53.9, 56.4, 62.8, 64.8, 79.8, 110.8, 127.7, 127.8, 128.6, 129.2, 129.9, 133.3, 135.67, 135.69, 135.9, 149.9, 163.6;

IR (KBr): v 3165, 3047, 2928, 1710, 1666, 1263, 1093, 700 cm$^{-1}$.

HRMS (ESI) calcd for C$_{33}$H$_{41}$N$_3$O$_4$Si (M+H)$^+$ 570.2788, found 570.2783.

7'-O-TBDPS-N-(phenylalanine methyl ester) morpholino thymine (7)

Overall yield 78% from starting material.

$^1$H NMR (500 MHz, CDCl$_3$): δ 0.97 (s, 9H), 1.81 (s, 3H), 2.27 (t, 1H, J=10.3 Hz), 2.44 (t, 1H, J=11.0 Hz), 2.74 (d, 1H, J=11.5 Hz), 2.88 (dd, 1H, J=13.3, 6.3 Hz), 2.98 (dd, 1H, J=13.0, 9.0 Hz), 3.11 (d, 1H, J=10.5 Hz), 3.48 (t, 1H, J=7.0 Hz), 3.55 (s, 3H), 3.64 (ddd, 2H, J=19.5, 11.0, 4.7 Hz), 3.78-3.80 (m, 1H), 5.62 (d, 1H, J=9.5 Hz), 7.11-7.15 (m, 3H), 7.16 (s, 1H), 7.22 (t, 2H, J=7.5 Hz), 7.27-7.30 (m, 4H), 7.33-7.35 (m, 2H), 7.56 (t, 4H, J=9.0 Hz), 8.88 (br s, 1H);

$^{13}$C NMR (75 MHz, CDCl$_3$): δ 12.6, 19.4, 27.1, 35.7, 50.7, 51.4, 53.3, 64.7, 68.9, 77.0, 80.3, 110.8, 126.8, 127.87, 127.89, 128.1, 128.2, 128.7, 129.2, 130.0, 130.5, 133.29, 133.33, 135.2, 135.6, 135.7, 135.9, 137.6, 149.99, 150.05, 163.8, 171.6;

IR (KBr): v 3068, 2929, 1691, 1465, 1267, 1111, 702 cm$^{-1}$.

HRMS (ESI) calcd for C$_{36}$H$_{44}$N$_3$O$_6$Si (M+H)$^+$ 642.2999, found 642.2968.

7'-O-TBDPS-N-propargyl-morpholino thymine (8)

Overall yield 71% from starting material.

$^1$H NMR (500 MHz, CDCl$_3$): δ 0.99 (s, 9H), 1.81 (s, 3H), 2.15 (t, 1H, J=10.5 Hz), 2.23 (t, 1H, J=2.5 Hz), 2.32 (t, 1H, J=11.0 Hz), 2.75 (d, 1H, J=11.5 Hz), 2.85 (d, 1H, J=10.5 Hz), 3.35 (d, 2H, J=1.5 Hz), 3.67 (dd, 1H, J=11.0, 5.0 Hz), 3.71 (dd, 1H, J=10.5, 4.5 Hz), 3.88-3.90 (m, 1H), 5.82 (dd, 1H, J=9.8, 2.8 Hz), 7.14 (s, 1H), 7.28-7.38 (m, 4H), 7.34-7.38 (m, 2H), 7.59 (td, 4H, J=8.3, 2.3 Hz), 8.75 (br s, 1H);

$^{13}$C NMR (75 MHz, CDCl$_3$): δ 12.5, 19.3, 26.8, 29.7, 46.5, 52.4, 54.7, 64.7, 74.3, 76.6, 77.4, 79.7, 110.77, 127.8, 129.9, 133.2, 133.3, 135.6, 135.7, 149.9, 163.6;

IR (KBr): v 3284, 3070, 2930, 1693, 1462, 1105, 702 cm$^{-1}$.

EXAMPLE 2

Figure 9:
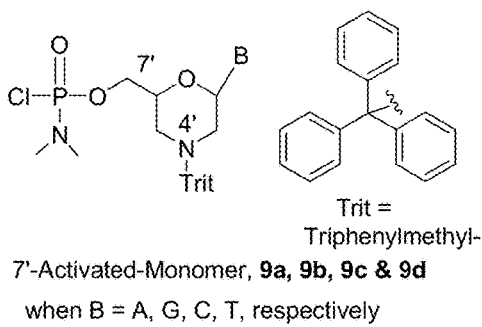
FIG. 9: illustrates the 7'-activated morpholino monomers for the synthesis of neutral (phosphorodiamidate) morpholino.
Figure 20:
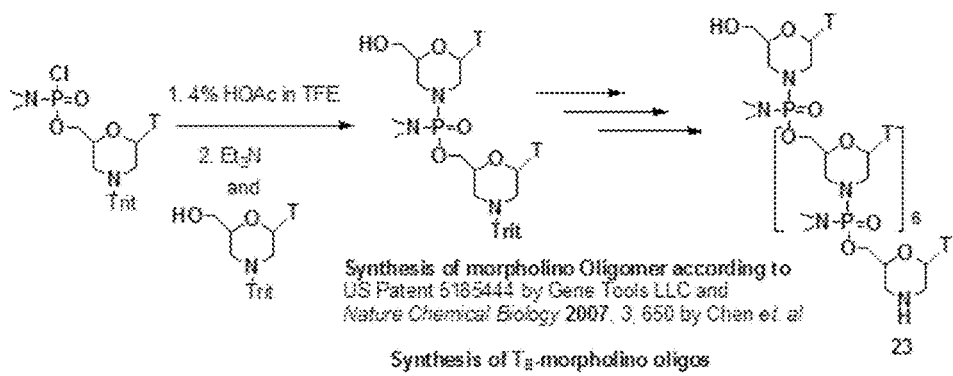
FIG. 20: illustrates the synthesis of T₈-morpholino oligos according to the procedure reported by U.S. Pat. No. 5,185,444, *Gene Tools LLC* and *Nature Chemical Biology* 2007, 3, 650 by Chen et. al.

Synthesis of 7'-Activated Monomers 9a, 9b, 9c & 9d in FIG. 9 and morpholino Oligomers 23 with Neutral Backbone in FIG. 1:

The 7'-activated monomers (FIG. 9) and morpholino oligomers (FIG. 1) were synthesized according to the procedure reported by Gene-Tools U.S. Pat. No. 5,185,444, 1993 and Chen, et. al. in *Nature Chemical Biology.* 2007, 3, 650 (FIG. 20).

EXAMPLE 3

Figure 10:
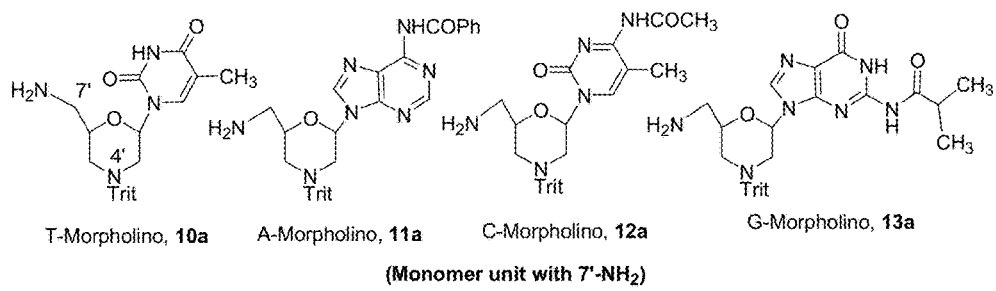
FIG. 10: illustrates the 7'-amino-modified morpholino monomers.
Figure 11:
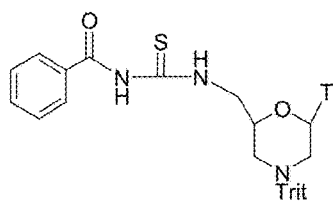
FIG. 11: illustrates the 7'-activated monomers for the synthesis of cationic morpholino.
Figure 12:
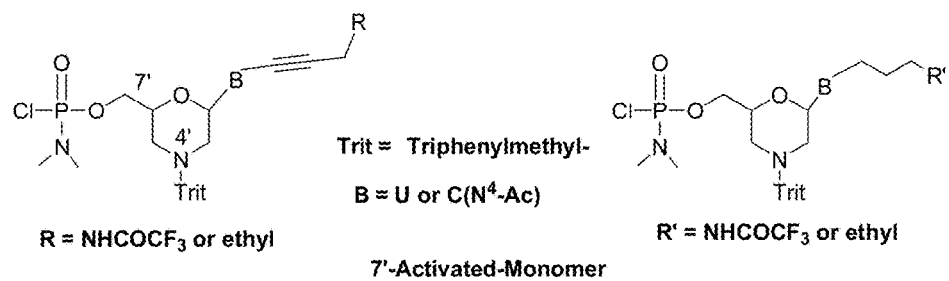
FIG. 12: illustrates 7'-activated (chlorophosphoramidate) morpholino monomers of 5-substituted pyrimidine bases with alkynyl and alkyl moieties (where R=ethyl or NHCOCF₃).
Figure 13:
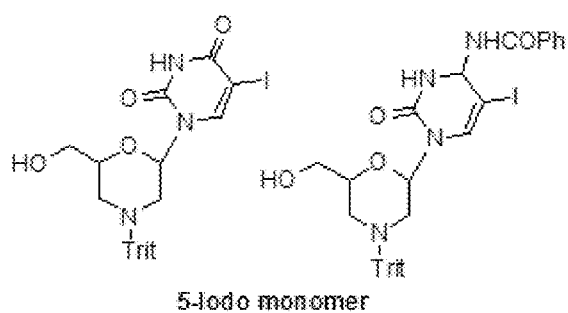
FIG. 13: illustrates the 5-iodo pyrimidines.
Figure 16:
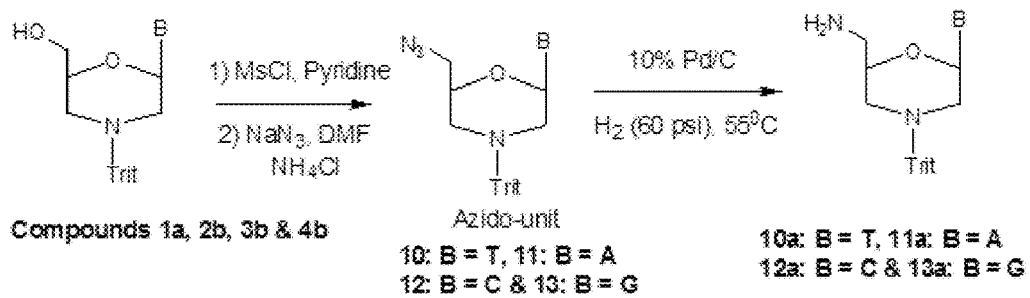
FIG. 16: illustrates the synthesis of 7'-amino-modified morpholino monomers.

Synthesis of 7'-amino Morpholino Monomers 10a, 11a, 12a & 13a in FIG. 10 which are Used for the Synthesis of Cationic-Morpholino-Oligomers The monomers 1a, 2b, 3b and 4b (reported in FIG. 8) (0.50 mmol) were treated with mesylchloride (0.60 mmol) in pyridine (10 ml) and the mesylated product was converted to the 7'-azido-unit in the presence of NaN$_3$ (1 mmol), DMF (10 ml) and NH$_4$Cl (1 mmol). The azide was converted to the corresponding amine (10a, 11a, 12a & 13a) by the reduction with 10% Pd/C/H$_2$ (60 psi) (FIG. 16). The overall yield was from 34-45% in this process.

EXAMPLE 4

Figure 17:
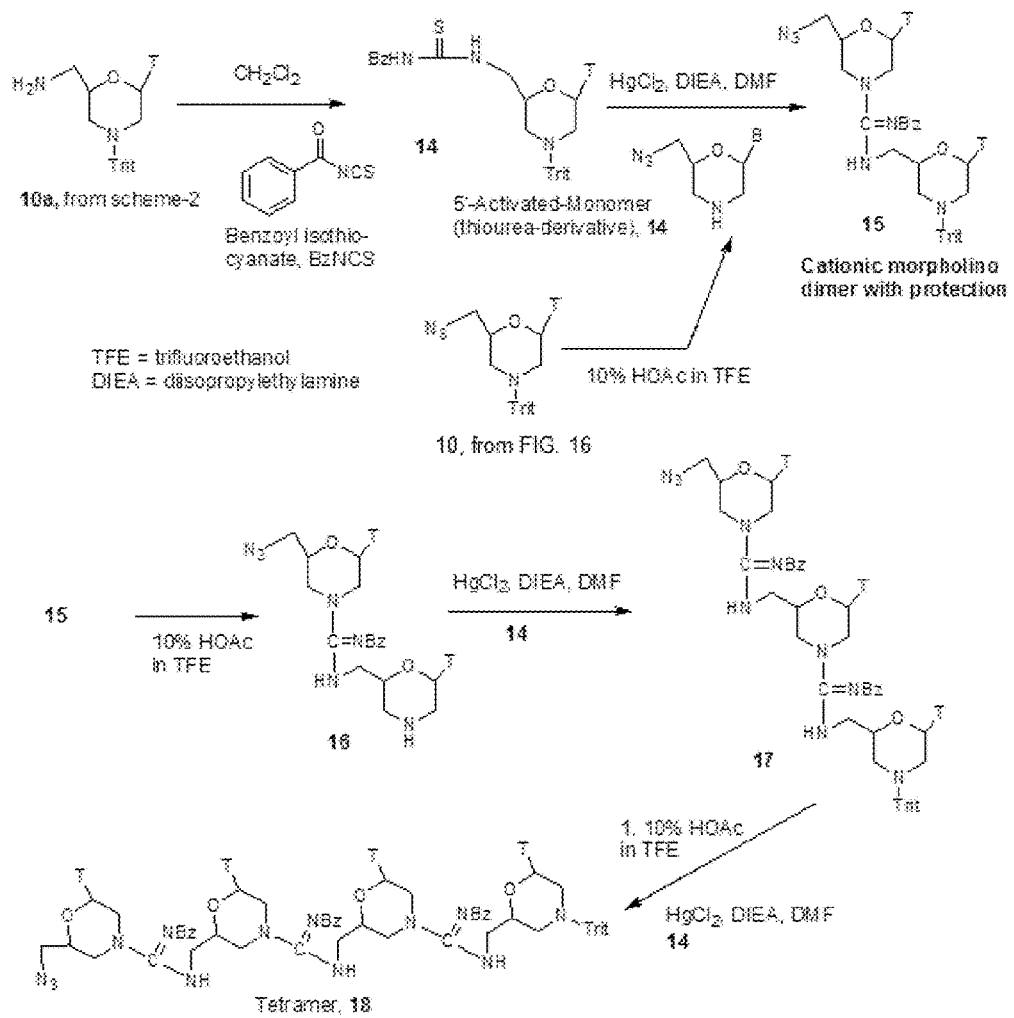
FIG. 17: illustrates the synthesis of cationic morpholino with the incorporation of guanidinium linkages in place of phosphorodiamidate linkages.

Synthesis of 7'-Activated Morpholino Monomer 14 (FIG. 11) and Synthesis of Cationic Morpholino (FIG. 2) with the Incorporation of Gaunidinium Linkages (FIG. 17)

The solution of 7'-amino monomer 10a (150 mg, 0.311 mmol) (see FIG. 16) in dichloromethane (DCM) was treated with benzoyl isothiocyanate (52 mg, 0.317 mmol). After 30 min, the solvent was evaporated and the residue was purified by silica gel column chromatography to obtain the activated monomer 14 (140 mg) in 70% yield and used in the next step for oligomer synthesis according to T. C. Bruice's method *Proc. Natl. Acad. Sci. USA.* 1994, 91, 7864.

The trityl group of monomer 10 (15 mg, 30 µmol) was deprotected with 10% HOAc in TFE. The reaction was monitored by TLC. After deprotection, the solvent was evaporated and the residue was dissolved in DMF. The activated monomer 14 (19 mg, 34 µmol) and freshly dried diisopropylethylamine (DIEA) (13 µL, 75 µmol) were then added and the solution was cooled to 0° C. A solution of HgCl$_2$ (10 mg, 38 µmol) in dry DMF was added drop wise and an instant cloudy white precipitate appeared. The reaction mixture was stirred for 1.5 h and diluted with a small amount of MeOH and was filtered through a short pad of celite and evaporated to dryness. The residue was dissolved in EtOAc, washed with water and brine, dried and concentrated. After purification by silica gel column chromatography, the product 15 (17 mg) was obtained in 68% yield.

Using the same reaction sequence (deprotection and coupling), the trimer 17 and tetramer 18 were synthesized, respectively. The product was purified by silica gel column chromatography and characterized by ESI mass spectroscopy (FIG. 17).

EXAMPLE 5

Synthesis of 7'-fluorophore-Conjugated Cationic Morpholino 20 (FIG. 3, FIG. 18)

To a solution of propargyl amine containing FITC (1.3 mg, 3.3 µmol) and tetramer 18 (2.7 mg, 1.7 µmol) was added 5 µL a solution of (1 mM TBTA-CuSO$_4$, 10 µL in DMSO and Na-ascorbate 10 µL in water) and was stirred for 15 hrs. The solvent was removed and purified by preparative TLC.

The trityl group was deprotected with 10% HOAc in TFE (100 µL) for 4 hrs. After removing the solvent, the free 4'-'NH was protected with acetyl group using acetic anhydride (5.1 µmol) and triethylamine (5.1 µmol).

The benzoyl groups were removed by K$_2$CO$_3$, MeOH and water (1:1) for three hours. The product 20 was purified by RP-HPLC (C18 column, elution with 3% aq. HOAc in acetonitrile). The compound (31% yield) was characterized by ESI mass spectroscopy (FIG. 18).

EXAMPLE 6

Figure 19:
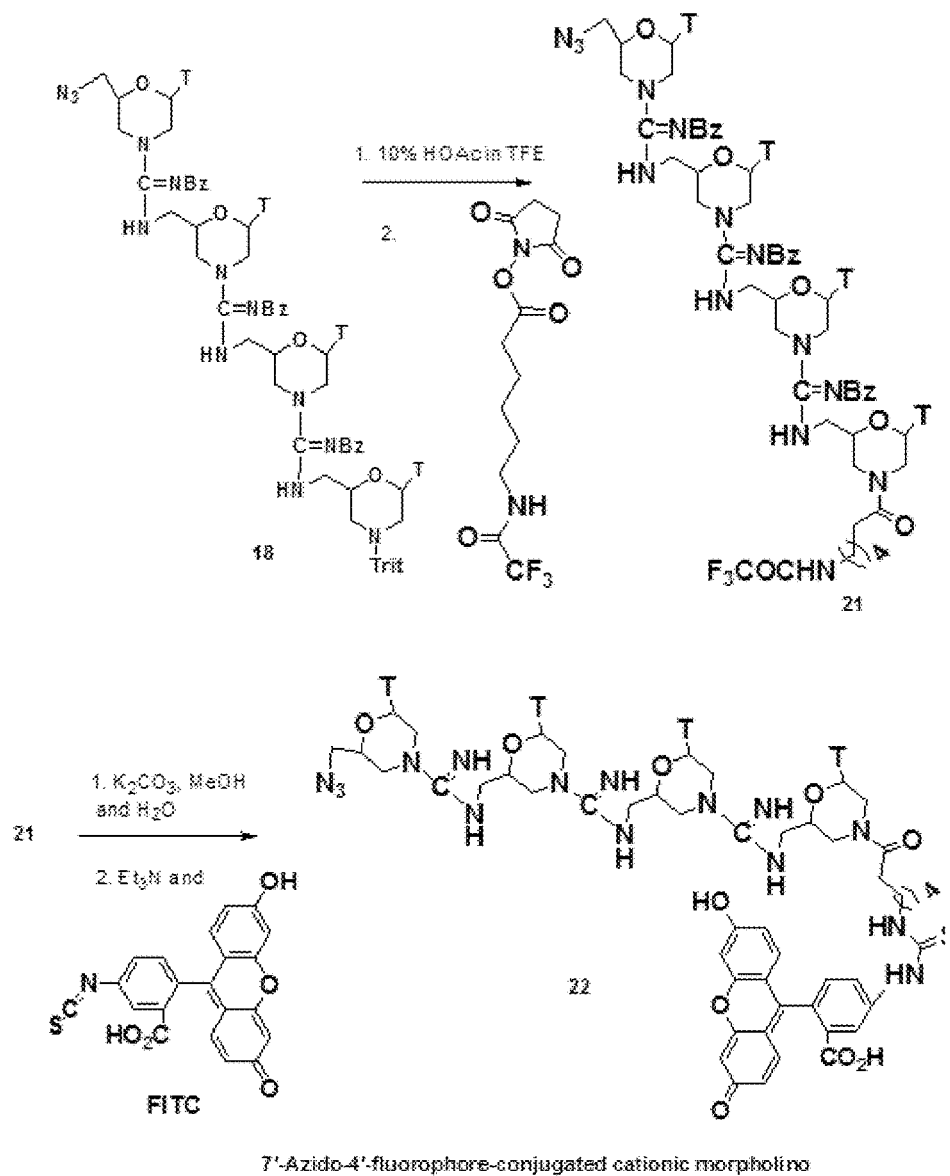
FIG. 19: illustrates the synthesis of 7'-azido-4'-fluorophore-conjugated cationic morpholino.

Synthesis of 7'-azido-4'-fluorophore-Conjugated Cationic Morpholino 22 (FIG. 4, FIG. 19):

The trityl group of 18 (2 mg, 1.23 μmol) was removed by 10% HOAc in TFE and the solvent was removed. The residue was dissolved in DMF and coupled with N-trifluoroacetyl aminocaproic acid N-hydroxysuccinimide ester (1.2 mg, 3.7 μmol) in the presence of $Et_3N$. The compound 21 was purified by preparative TLC and the benzoyl and trifluoroacetyl groups were removed by 5% $K_2CO_3$ in MeOH and water (1:1). The same solution was used for the coupling with FITC. The compound 22 was purified by HPLC (C18 column, elution with 3% HOAc in acetonitrile). The compound (33% yield) was characterized by ESI mass spectroscopy (FIG. 19).

EXAMPLE 7

Figure 21:
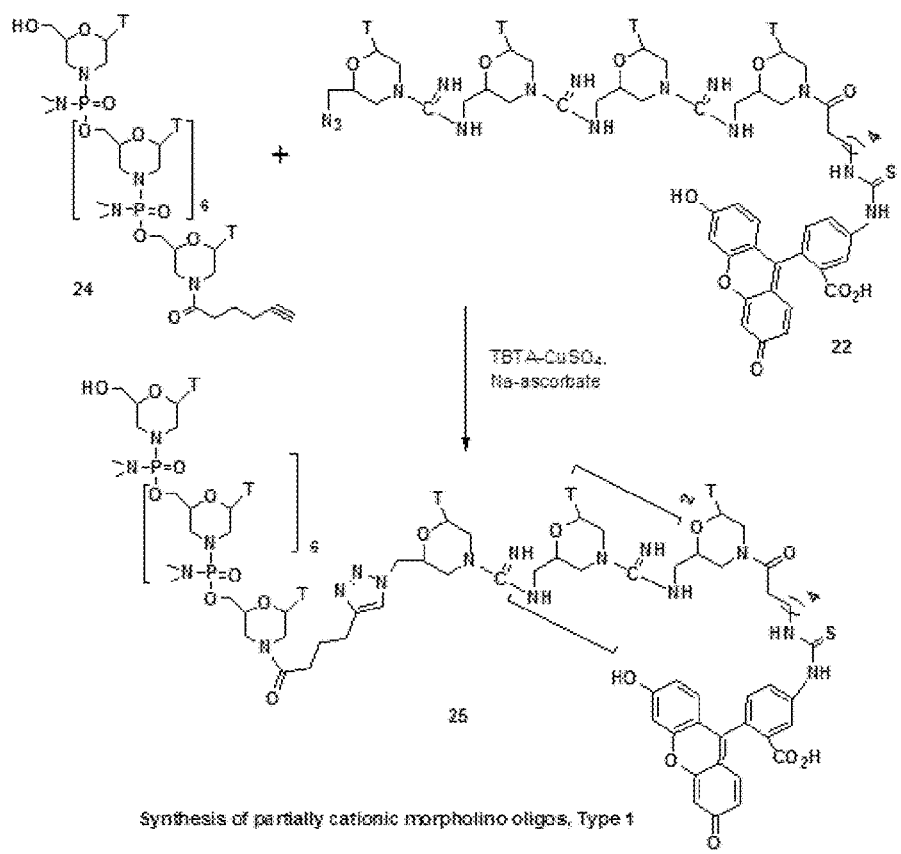
FIG. 21: illustrates the synthesis of partially cationic morpholino oligos, Type-1.

Synthesis of Partially Cationic Morpholino 25 by the Conjugation of Cationic Morpholino with Neutral Morpholino (FIG. 5, FIG. 21)

The compound 23 ($T_8$-morpholino) (10 mg, 3.8 μmol) obtained in FIG. 20 was treated with N-hydroxysuccinimide ester of hexynoic acid (12 μmol) in the presence of $Et_3N$ in DMF to obtain the compound 24 which was triturated with ether and ethylacetate to remove unwanted reagents. This was then conjugated with 7'-azido-fluorophore-conjugated morpholino 22 by click reaction. The partially cationic morpholino 25 (Type 1) was then dried and triturated with MeOH. After trituration, the residue was dissolved in aq. $NH_4OH$ to pH 8 and loaded in cation exchange resin column (Dowex resin) and washed with water, MeOH then elution with 50% aq. $NH_4OH$, in MeOH. The yellowish green color solution was then loaded into Q-Sepharose fast flow column and elution was with 2% HOAc in water. The solvent was removed in reduced pressure and dissolved in 10% aq. $NH_4OH$ solution. The compound 25 was obtained in 55% yield calculated based on a UV-VIS spectrometer ($\lambda$=493 nm, $\epsilon$=93,000 cm$^{-1}$ M$^{-1}$) and was characterized by ESI mass spectroscopy (FIG. 21).

EXAMPLE 8

Figure 22:
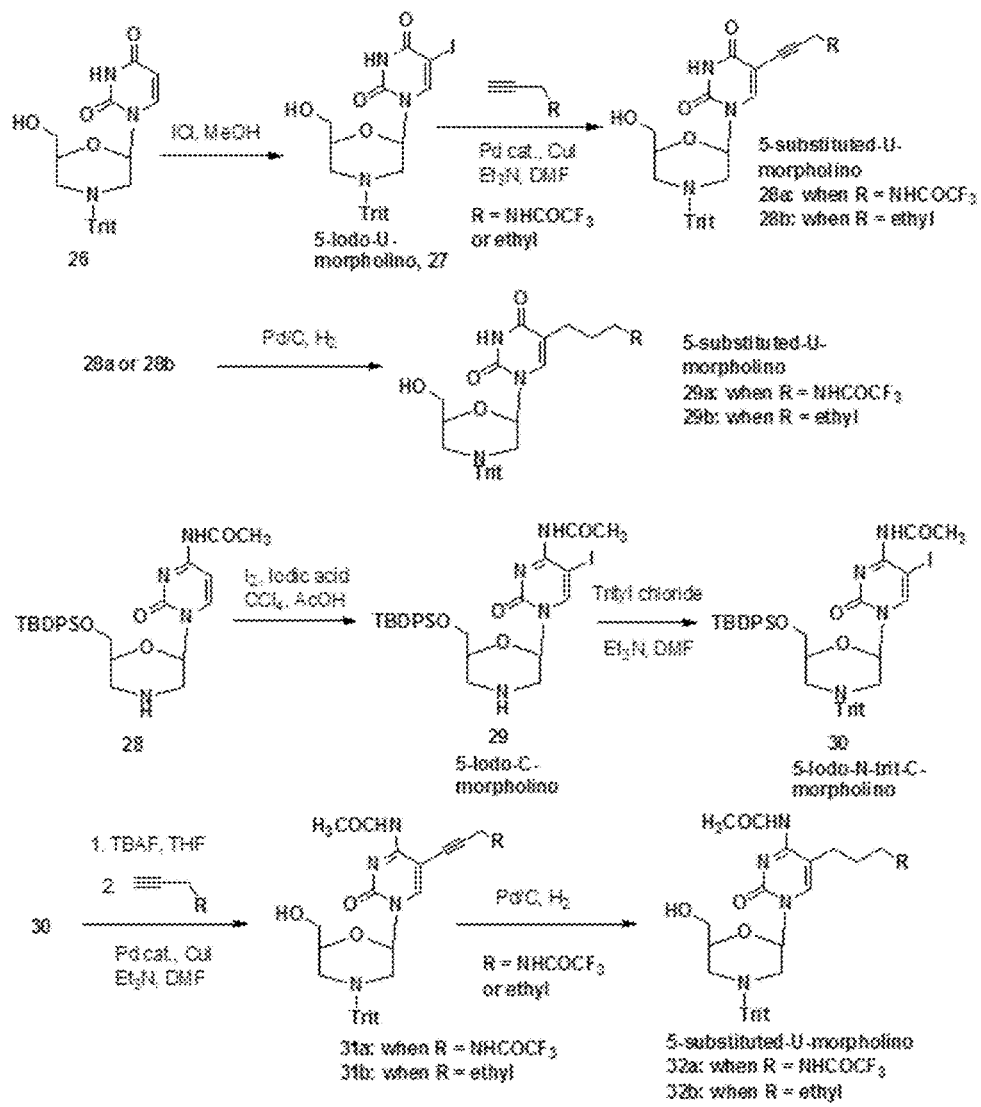
FIG. 22: illustrates the synthesis of 5-iodo and 5-substituted pyrimidines of morpholino monomers.

Synthesis of 5-iodo-N-trit-U-morpholino Monomer (27) (FIG. 22)

The N-trit-U-morpholino 26 was treated with ICl in MeOH and the reaction was monitored by TLC. The solvent was removed and dissolved in dichloromethane (DCM), washed with 5% aq. sodium bicarbonate, sodium thiosulfate and brine. The solvent was removed and dissolved in dry DCM and treated with $Et_3N$ (1.5 equiv) and the iodo compound 27 was purified by column chromatography and characterized.

EXAMPLE 9

Synthesis of 7'-TBDPS-5-iodo-N-trit-C(N4-Ac)-morpholino Monomer (30) (FIG. 22)

The compound 28 was treated with $I_2$, iodic acid in $CCl_4$ and HOAc (1:1) and stirred at room temperature for 40 hrs. The compound 29 was extracted in dichloromethane and dried. It was then protected with trityl group in the presence of trityl chloride and $Et_3N$ in DMF. The compound 30 was then purified by column chromatography and characterized.

EXAMPLE 10

Alkynylation and Alkylation for the Preparation of Compounds 28a, 28b, 29a, 29b, 31a, 31b, 32a, 32b (FIG. 22)

The alkynylation was done according to the procedure reported by Hobbs, F. W. *J. Org. Chem.* 1989, 54, 3420 and the alkyne group was reduced in the presence of 10% Pd/C/$H_2$ in 1 atm pressure. All these compounds were purified by column chromatography on silica gel and characterized.

EXAMPLE 11

Figure 23:
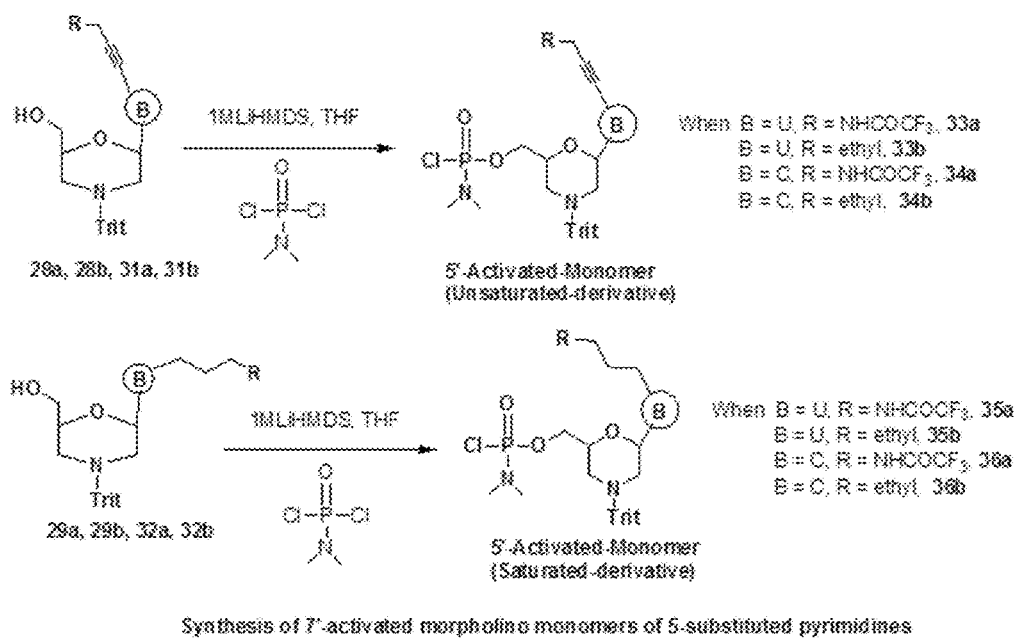
FIG. 23: illustrates the synthesis of 7'-activated (chlorophosphoramidate) morpholino monomers of 5-substituted pyrimidines with alkynyl and alkyl moieties (where R=CH₃CH₂ or NHCOCF₃).
Figure 24:
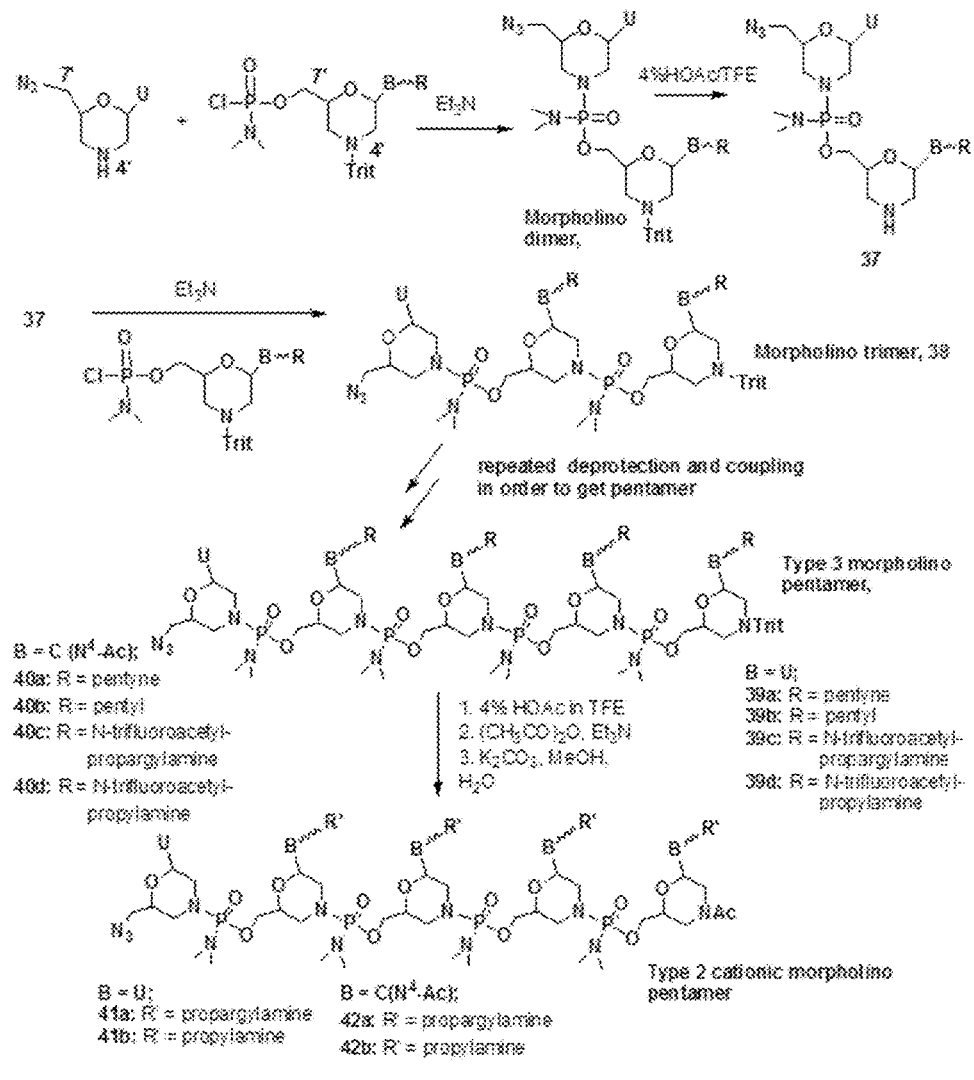
FIG. 24: illustrates the synthesis of cationic morpholino oligos (Type 2) with the incorporation of 5-substituted pyrimidines. It also includes the modified neutral morpholino oligos (Type 3).

Synthesis of 7'-Activated Morpholino Monomers of 5-Substituted Pyrimidines 33a, 33b, 34a, 34b, 35a, 35b, 36a, 36b (FIG. 12, FIG. 23) and the Morpholino Oligos, Type 2 and Type 3 (FIG. 6 and FIG. 24)

The 7'-activated monomers (FIG. 12) and the morpholino oligos were synthesized according to the procedure reported by Gene-Tools U.S. Pat. No. 5,185,444, 1993 and Chen, et. al. in *Nature Chemical Biology.* 2007, 3, 650 (FIG. 23 and 24).

The morpholino oligomers (pentamer, 39a, 39b, 39c, 39d and 40a, 40b, 40c, 40d) were purified by preparative TLC and obtained in pure form.

Detritylation of 39c, 39d and 40c, 40d by 4% HOAc in TFE followed by acetylation by acetic anhydride/$Et_3N$ and deprotection of trifluoroacetyl groups by $K_2CO_3$, MeOH, $H_2O$ (1:1) gave the oligos such as: 41a, 41b and 42a, 42b, respectively and purified by passing through cation exchange resin (Dowex). The compound was eluted with 20% $NH_4OH$ in methanol and fractions were analyzed with a UV-VIS spectrometer ($\lambda$=260 nm) and characterized by ESI-MS (FIG. 24).

EXAMPLE 12

Figure 25:
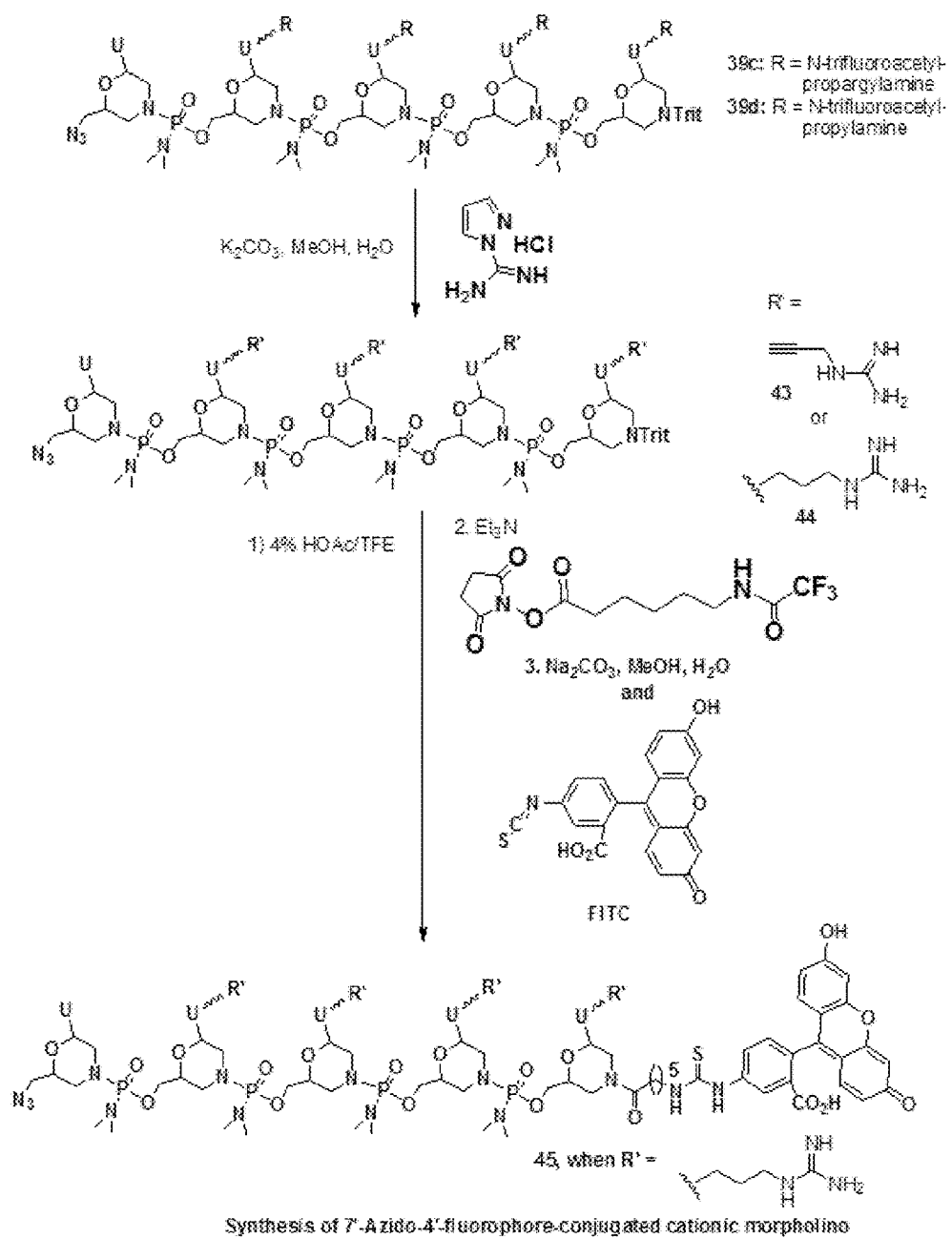
FIG. 25: illustrates the synthesis of cationic morpholino (Type 2) with the incorporation of 5-substituted uridine and 4'-conjugated-fluorophore.

Synthesis of Type 2 Cationic Morpholinos: Introduction of Cationic Charge by Guanidinium Groups to the Pyrimidine Bases and Conjugated with Fluorophore at 4'-End (FIG. 25)

The pentamer 39c or 39d (5 μmol) was treated with $K_2CO_3$ in MeOH/$H_2O$ (1:1). The free amine containing morpholinos was then converted to the guanidinium groups using the methodology reported by Wender, P. et. al. *Org. Lett.* 2001, 3, 3232 to obtain 43 or 44. The solvent was removed and the dry mass was washed with acetonitrile and dried. The compound 44 was then treated with 4% HOAc/TFE to remove trityl group. It was dried and washed with acetonitrile and the dry mass was dissolved in DMF/$Et_3N$ mixture and treated with N-trifluoroacetyl-amino caproic acid N-hydroxysuccinimide ester (10 μmol). After 14 hrs, the solvent was removed and washed with acetonitrile. The residue was then dissolved in MeOH/$H_2O$ mixture in the presence of $Na_2CO_3$ and treated with FITC and the fluorophore-conjugated material was purified by cation exchange resin (Dowex), elution was with 50% $NH_4OH$ in MeOH to obtain 45. The compound 45 was obtained in 40% yield calculated based on a UV-VIS spectrometer ($\lambda$=493 nm, $\epsilon$=93,000 cm-$^1$ M$^{-1}$) and was characterized by ESI mass spectroscopy (FIG. 25).

EXAMPLE 13

Cellular Transfection Properties of Fluorophore-Conjugated Cationic Morpholinos in Hela Cell Tissue culture was carried out at 37° C. in a humidified atmosphere of 5% carbon dioxide and 95% air.

HeLa cells were grown in 2×10-cm dishes, each of which contained 9 mL of 10% fetal bovine serum (FBS)-supplemented Dulbecco's Modified Eagle Medium (DMEM). After two days, cells were trypsinized and made a pellet and the cells were dispersed in 24 mL same media and subcultured in 24-well plate (1 mL/well). After 15 hrs, the fluorophore-conjugated morpholino 20 was added in varying concentrations (7.5, 15, 37.5, 75, 150, 375, 750 and 1500 nM) and cells were incubated at 37° C. for 15 hrs until 40% confluency. After removal of medium, the cells were Washed twice with 1 mL phosphate buffered saline at pH 7.4 (PBS) and were observed under fluorescence microscopy, OLYMPUS IX-51.

EXAMPLE 14

In Vivo Testing of the Compounds Using Zebrafish (*Danio rerio*) as a Model Organism The morpholinos of the present invention is tested in whole embryo assays in zebrafish wherein the fertilized eggs are transferred into water containing morpholino oligos in effective concentrations and observed its transfection properties during development (24 hpf, hr post fertilization).

It is thus possible by way of the present invention to provide for new and improved highly stable partially cationic/completely neutral morpholino-based antisense agent might be having higher activity and selectivity with regard to better transfection efficiency and more specific gene regulation and its method of synthesis. As discussed hereinbefore the said method of synthesis to achieve the product of the invention is easy, fast, cost-effective in involving lesser number of ingredients in the said synthetic steps. The improved partially cationic morpholino-based antisense agent of the present invention is advantageously soluble in culture medium and is sufficient for cell penetration thus eliminating the need for injecting the antisense agents into the cells. Also, it is possible by way of the present invention to achieve the synthesis of the new cationic morpholino-based antisense agents that are conjugated to dyes, fluorophore and drug molecules to facilitate the study of their cellular transfection properties and open up avenues for new synthetic methodology for the synthesis of morpholino monomers.

We claim:

1. Morpholino based oligomers suitable as antisense agents comprising:
    one or more cationic backbone having phosphorodiamidate linkage and further guanidinium linkage as replacement of some of said phosphorodiamidate linkage wherein a purine and/or pyrimidine base of the morpholino unit in said cationic backbone contains one or more substituents selected from the group consisting of alkynyl, trifluoroacetylamide, alkylamine, and guanidinium.

2. The morpholino based oligomers according to claim 1 wherein the oligomer is soluble in culture medium and sufficient for cell penetration on its own.

3. The morpholino based oligomers according to claim 1 wherein
    (i) said oligomers having guanidinium linkage are synthesized from monomers selected from the group consisting of:

(10a)

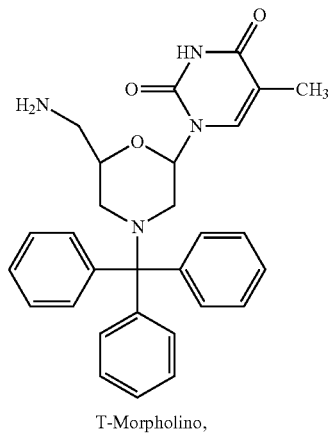

T-Morpholino, 1-(6-(aminomethyl)-4-tritylmorpholin-2-yl)-5-methylpyrimidine-2,4(1H,3H)-dione (11a)

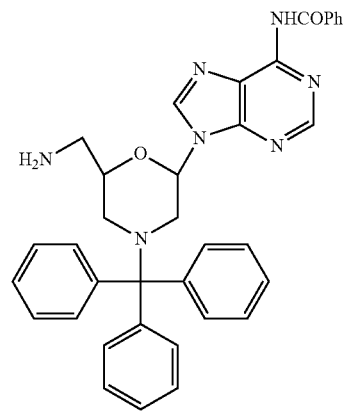

A-Morpholino,

N-(9-(6-(aminomethyl)-4-tritylmorpholin-2-yl)-9H-purin-6-yl)benzamide (12a)

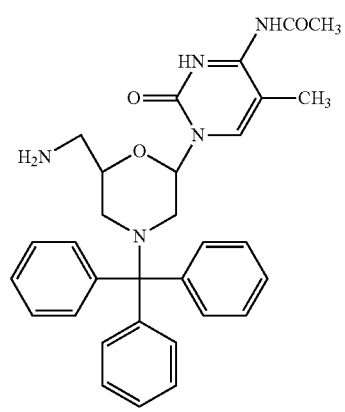

C-Morpholino,

N-(1-(6-(aminomethyl)-4-tritylmorpholin-2-yl)-5-methyl-2-oxo-1,2-dihydropyrimidin-4-yl)acetamide -continued

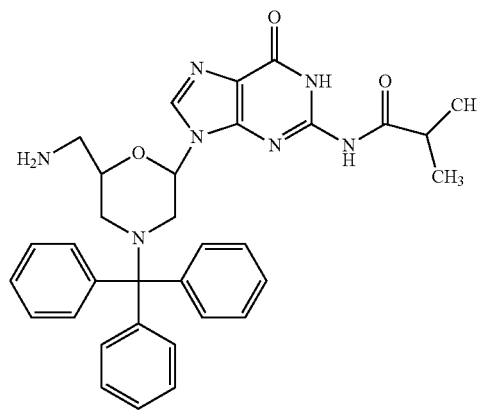

G-Morpholino,
N-(9-(6-(aminomethyl)-4-tritylmorpholin-2-yl)-
6-oxo-6,9-dihydro-1H-purin-2-yl)isobutyramide (13a)

and

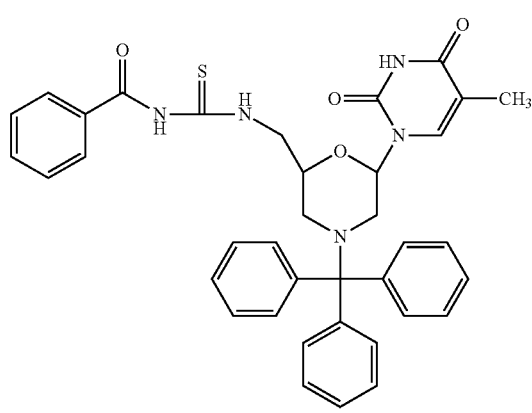

7'-Activated-Monomer
(thiourea-derivative),

N-((6-(5-methyl-2,4-dioxo-3,4-dihydropyrimidin-
1(2H)-yl)-4-tritylmorpholin-2-yl)methylcarbamothioyl)benzamide (14)

ii) said oligomers having phosphorodiamidate linkage are synthesized from monomers selected from the group consisting of:

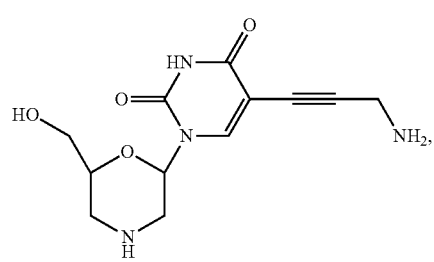

5-(3-aminoprop-1-ynyl)-1-(6-
(hydroxymethyl)morpholin-2-yl)pyrimidine-
2,4(1H,3H)-dione (1.1)

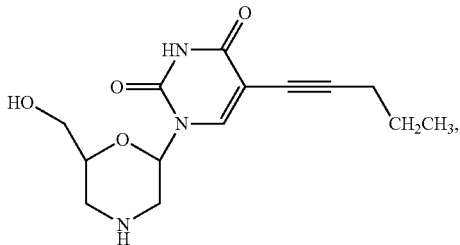

1-(6-(hydroxymethyl)morpholin-2-yl)-5-(pent-1-
ynyl)pyrimidine-2,4(1H,3H)-dione (1.2)

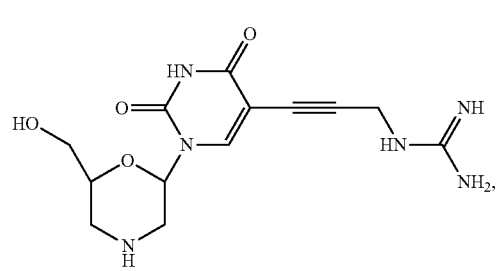

1-(3-(1-(6-(hydroxymethyl)morpholin-2-yl)-2,4-dioxo-1,2,3,4-
tetrahydropyrimidin-5-yl)prop-2-ynyl)guanidine (1.3)

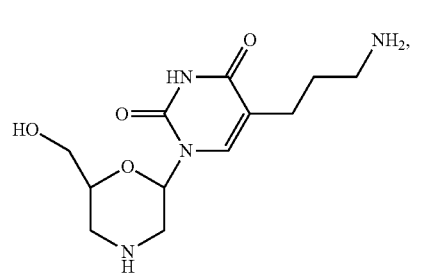

5-(3-aminopropyl)-1-(6-(hydroxymethyl)morpholin-2-
yl)pyrimidine-2,4(1H,3H)-dione (1.4)

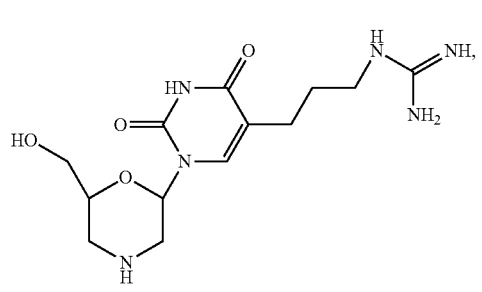

1-(3-(1-(6-(hydroxymethyl)morpholin-2-yl)-2,4-dioxo-
1,2,3,4-tetrahydropyrimidin-5-yl)propyl)guanidine (1.5)

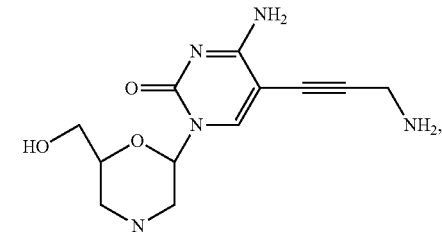

4-amino-5-(3-aminoprop-1-ynyl)-1-
(6-(hydroxymethyl)morpholin-2-yl)pyrimidin-2(1H)-one (3.1)

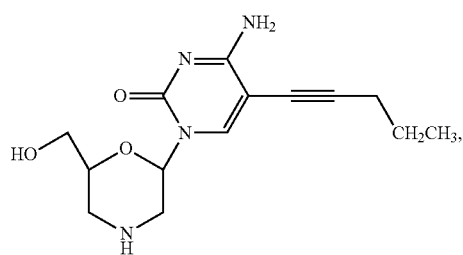

4-amino-1-(6-(hydroxymethyl)morpholin-2-yl)-
5-(pent-1-ynyl)pyrimidin-2(1H)-one
(3.2)

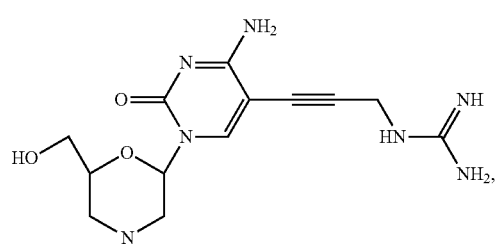

1-(3-(4-amino-1-(6-(hydroxymethyl)morpholin-2-yl)-
2-oxo-1,2-dihydropyrimidin-5-yl)prop-2-ynyl)guanidine
(3.3)

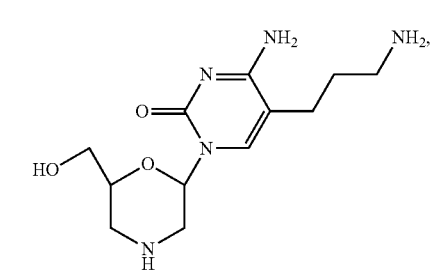

4-amino-5-(3-aminopropyl)-1-(6-(hydroxymethyl)
morpholin-2-yl)pyrimidin-2(1H)-one
(3.4)

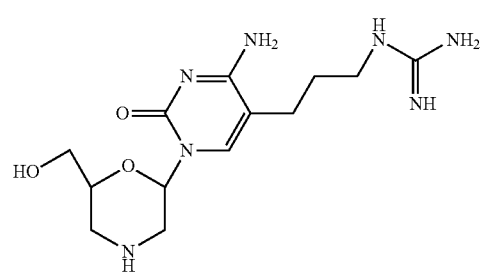

1-(3-(4-amino-1-(6-(hydroxymethyl)morpholin-2-yl-
2-oxo-1,2-dihydropyrimidin-5-yl)propyl)guanidine
(3.5)

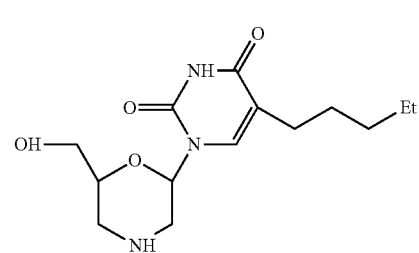

1-(6-(hydroxymethyl) morpholin-2-yl)
-5-pentylpyrimidine-2,4(1H,3H)-dione
(1.51)

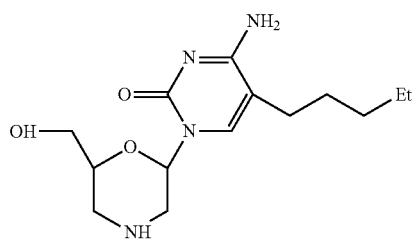

4-amino-1-(6-(hydroxymethyl)morpholin-2-
yl)-5-pentylpyrimidin-2(1H)-one
(3.51)

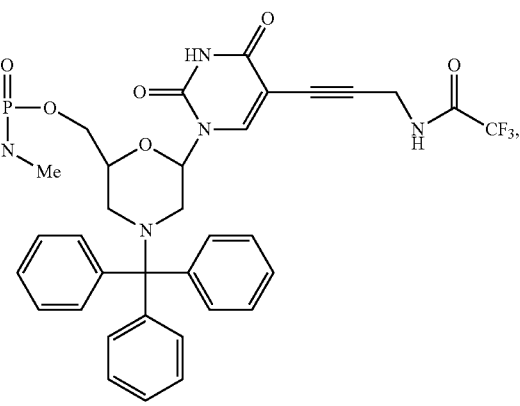

(6-(2,4-dioxo-5-(3-(2,2,2-trifluoroacetamido)prop-1-
ynyl)-3,4-dihydropyrimidin-1(2H)-yl)-4-tritylmorpholin-
2-yl)methyl dimethylphosphoramidochloridate
(1.6)

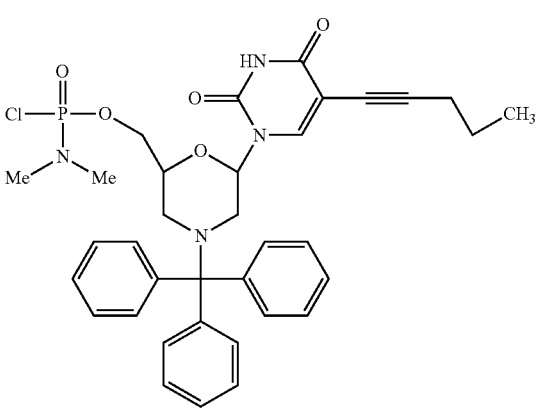

(6-(2,4-dioxo-5-(pent-1-ynyl)-3,4-dihydropyrimidin-
1(2H)-yl)-4-tritylmorpholin-2-yl)methyl
dimethylphosphoramidochloridate
(1.7)

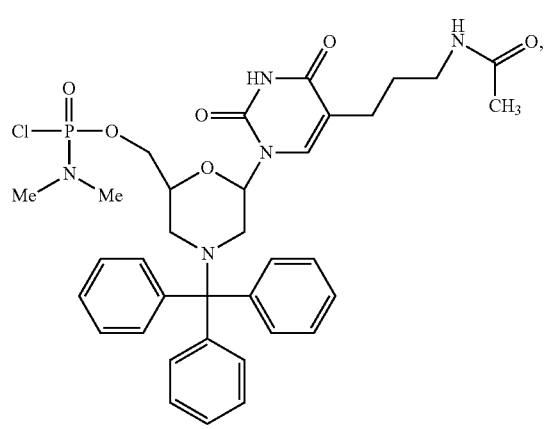

(6-(2,4-dioxo-5-(3-(2,2,2-trifluoroacetamido)propyl)-3,4-dihydropyrimidin-1(2H)-yl)-4-tritylmorpholin-2-yl)methyl dimethylphosphoramidochloridate (1.8)

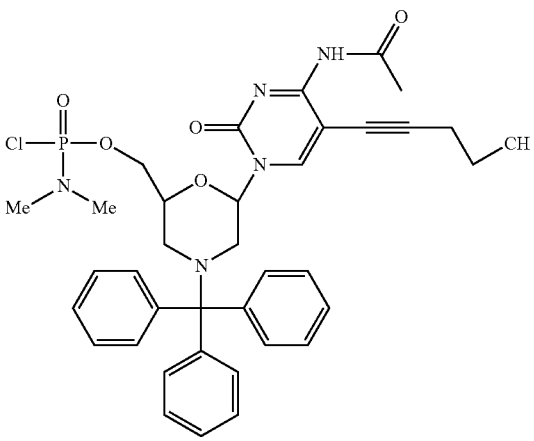

(6-(4-acetamido-2-oxo-5-(pent-1-ynyl)pyrimidin-1(2H)-yl)-4-tritylmorpholin-2-yl)methyl dimethylphosphoramidochloridate (3.7)

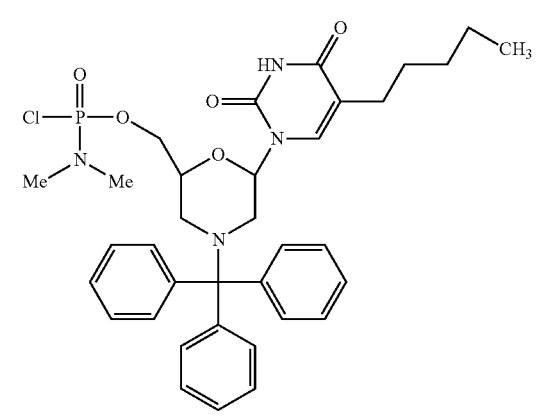

(6-(2,4-dioxo-5-pentyl-3,4-dihydropyrimidin-1(2H)-yl)-4-tritylmorpholin-2-yl)methyl dimethylphosphoramidochloridale (1.9)

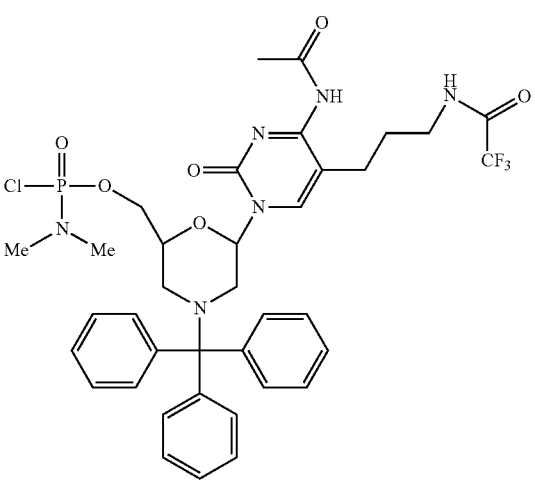

(6-(4-acetamido-2-oxo-5-(3-(2,2,2-trifluoroacetamido)propyl)pyrimidin-1(2H)-yl)-4- and (3.8)

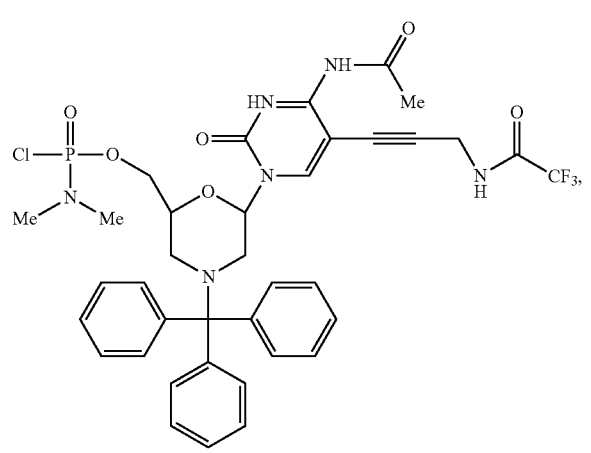

(6-(4-acetamido-2-oxo-5-(3-(2,2,2-trifluoroacetamido)prop-1-ynyl)pyrimidin-1(2H)-yl)-4-tritylmorpholin-2-yl)methyl dimethylphosphoramidochloridale (3.6)

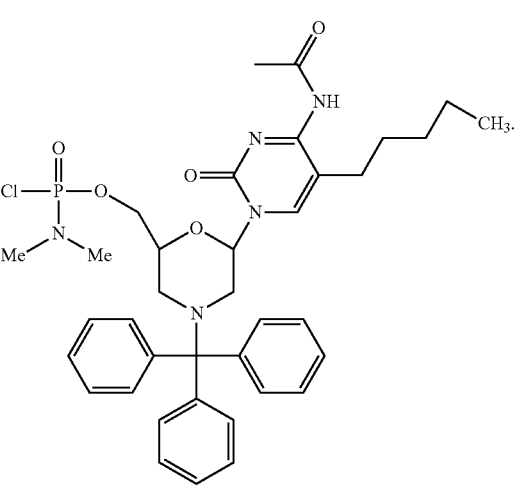

(6-(4-acetamido-2-oxo-5-pentylpyrimidin-1(2H)-yl)-4-tritylmorpholin-2-yl(methyl dimethylphosphoramidochloridate (3.9)

4. The morpholino based oligomers suitable as antisense agents according to claim 1 wherein the length of the said oligomers is up to 25-mers that does not affect the Watson-Crick base pairing, has target specificity and selectivity and avoids the need of conjugation with arginine rich peptides.

5. The morpholino based oligomers suitable as antisense agents according to claim 1 wherein said oligomer is conjugated at the 4' end and/or the 7' end of the morpholino backbone selectively with biomolecules, drugs, or dyes selected from fluorophores adapted to facilitate cellular transfection properties and monitoring of transfection efficiency.

\* \* \* \* \*